US010457639B2

(12) United States Patent
Brown et al.

(10) Patent No.: US 10,457,639 B2
(45) Date of Patent: Oct. 29, 2019

(54) FLUORESCENT REGULATORS OF RASSF1A EXPRESSION AND HUMAN CANCER CELL PROLIFERATION

(75) Inventors: Milton L. Brown, Brookeville, MD (US); Kathryn D. Sheikh, Washington, DC (US); Mikell A. Paige, Fairfax, VA (US); Partha Banerjee, Rockville, MD (US); Shankar Jagadeesh, Gaithersburg, MD (US)

(73) Assignee: GEORGETOWN UNIVERSITY, Washington, DC (US)

( * ) Notice: Subject to any disclaimer, the term of this patent is extended or adjusted under 35 U.S.C. 154(b) by 0 days.

(21) Appl. No.: 13/059,183

(22) PCT Filed: Aug. 14, 2009

(86) PCT No.: PCT/US2009/004681
§ 371 (c)(1),
(2), (4) Date: Feb. 15, 2011

(87) PCT Pub. No.: WO2010/019271
PCT Pub. Date: Feb. 18, 2010

(65) Prior Publication Data
US 2011/0152339 A1 Jun. 23, 2011

Related U.S. Application Data

(60) Provisional application No. 61/189,059, filed on Aug. 15, 2008.

(51) Int. Cl.
*C07D 209/88* (2006.01)
*A61K 31/403* (2006.01)
*A61K 45/06* (2006.01)

(52) U.S. Cl.
CPC .......... *C07D 209/88* (2013.01); *A61K 31/403* (2013.01); *A61K 45/06* (2013.01)

(58) Field of Classification Search
CPC ..... C07D 209/88; A61K 31/403; A61K 45/06
See application file for complete search history.

(56) References Cited

U.S. PATENT DOCUMENTS 3,966,703 A * 6/1976 Bleck et al. .................. 534/662
5,677,328 A 10/1997 Takaki

FOREIGN PATENT DOCUMENTS

| CA | 2575046 | 2/2006 |
|----|---------|--------|
| CA | 2719457 | 10/2009 |
| EP | 0679641 | 11/1995 |
| EP | 1184373 | 3/2002 |
| EP | 1238973 | 9/2002 |
| EP | 1352650 | 10/2003 |
| EP | 1918711 | 5/2008 |
| WO | 9402483 | 2/1994 |
| WO | 9932463 | 7/1999 |
| WO | 0183452 | 11/2001 |
| WO | 2002006255 | 1/2002 |
| WO | 2002060867 | 8/2002 |
| WO | 02074306 | 9/2002 |
| WO | 2005016922 | 2/2005 |
| WO | 2006002908 | 1/2006 |
| WO | 2007014687 | 2/2007 |
| WO | 2007036131 | 4/2007 |
| WO | 2007042912 | 4/2007 |
| WO | 2009086472 | 7/2007 |
| WO | 2007026203 | 8/2007 |
| WO | 2008051523 | 5/2008 |
| WO | WO 2008/051523 | * 5/2008 ........... A61K 31/403 |

OTHER PUBLICATIONS

Manjunath (CAPLUS Abstract of: Quarterly Journal of the Indian Chemical Society, (1927), 4, 271-82).*
Goetz (CAPLUS Abstract of: Journal of Heterocyclic Chemistry (1974), 11(3), 445-7).*
Bard et al. (CAPLUS Abstract of: Journal of Physical Chemistry (1980), 84(10), 1262-6).*
Schmidt (CAPLUS Abstract of: U.S. Pat. No. 3,046,121).*
Myoshi et al. (CAPLUS Abstract of: WO 9725311(1997)).*
Arch (CAPLUS Abstract of: WO 2000027434 (2000)).*
Thornber (Chem. Soc. Rev., 1979, v. 8, p. 563-580).*
Hayashi et al. (CAPLUS Abstract of WO 2007102392 (Sep. 13, 2007)).*
Arnim, et al., "Synthesis and phase behavior of new carbazole containing liquid crystal side chain polysiloxanes", Macro Chem. Physics, 197(9):2729-43 (1996).
Beaulieu, et al., "An essential role for DNA methyltransferase DNMT3B in cancer cell survival", J Biol. Chem., 31:28176-81 (2002).
Brueckner, et al., "Epigenetic reactivation of tumor suppressor genes by a novel small-molecule inhibitor of human DNA methyltransferases", Cancer Res., 65:6305-6311 (2005).
Chen, et al., "Increased cell growth and tumorigenicity in human prostate LNCaP cells by overexpression to cyclin D1", Oncogene., 16: 1913-1920 (1998).
Donninger, et al., "The RASSF1A tumor suppressor", J of Cell Sci., 120:3163-72 (2007).
Freeman, et al., "Triphenylphosphine-mediated reductive cyclization of 2-nitrobiphenyls: a practical and convenient synthesis of carbazoles" J. Org. Chem., 70:5014-19 (2005).
International Search Report PCT/US2009/004681 dated Dec. 10, 2009.
Isaacs, "Role of androgens in prostatic cancer", Vitam Horm., 49: 433-502 (1994).
Ito, et al., "New carbazole alkaloids from murraya euchrestifolia", Chem. Pharma. Bul., 39(7):1668-71 (1991).

(Continued)

*Primary Examiner* — Robert H Havlin
(74) *Attorney, Agent, or Firm* — Pabst Patent Group LLP

(57) ABSTRACT

The invention provides methods for the treatment of cancer in a subject comprising administering a dansyl-carbazole compound.

20 Claims, 9 Drawing Sheets
Specification includes a Sequence Listing.

(56) References Cited

OTHER PUBLICATIONS

Itoigawa, et al., "Antitumor agents 203 carbazole alkaloid murrayaquinone A and related synthetic carbazolequinones as cytotoxic agents", J Natl. Prod., 63 (7):893-97 (2000).

Jagadeesh, et al., "Mahnine reverses an epifentically silenced tumor suppressor gene RASSFIA in human prostate cancer", Biochem. Biophy. Res. Comm., 362:212-17 (2007).

Kim, et al., "Co-operation and communication between the human maintenance and de novo DNA (cytosine-5) methyltransferases", EMBO J, 21:4183-95 (2002).

Kuzmin, et al., "The RASSF1A tumor suppressor gene is inactivated in prostate tumors and suppresses growth of prostate carcinoma cells", Cancer Res., 62: 3498-3502 (2002).

Li, et al., "DNA methylation in prostate cancer", Biochim. Biophys. Acta., 1704:87-102 (2004).

Liu, et al., "Frequent hypermethylation of the RASSF1A gene in prostate cancer", Oncogene., 21:6835-40 (2002).

Lyko, et al., "DNA methyltransferase inhibitors and the development of epigenetic cancer therapies", J Natl. Cancer Inst., 97:1498-1506 (2005).

Majumder, et al., "Role of de novo DNA methyltransferases and methyl CpG-binding proteins in gene silencing in a rat hepatoma", J of Biol. Chem., 277:16048-58 (2002).

Martinez-Palau, et al., "Synthsis of luminescent N-arylcarbazoles by cooper bronze-mediated reaction", Lett Org. Chem, 1:231-37 (2004).

Musgrove, et al., "Cyclin D1 induction in breast cancer cells shortens G1 and is sufficient for cells arrested in G1 to complete the cell cycle", PNAS, 91:8022-26 (1994).

Nakahara, et al., "Antimutagenicity of Some edible thai plants and a bioactive carbazole alkaloid, mahanine, isolated from micromelum minutum", J Agric. Food Chem., 50:4796-4802 2002).

Pfeifer, et al., "Methylation of the RASSF1A gene in human cancers", Biol Chem., 383:907-14 (2002).

Rong, et al., "Tumor suppressor RASSF1A is a microtubule-binding protein that stabilizes microtubules and induces G2/M arrest", Oncogene, 23: 8216-8230 (2004).

Roy, et al., "Mahanine, a carbazole alkaloid from micromelum minutum, inhibits cell growth and induces apoptosis in U937 cells through a mitochondrial dependent pathway", Bri J Pharamacology, 145:145-155 (2005).

Roy, et al., "Mechanism of mahanine-induced apoptosis in human leukemia cells (HL-60)", Biochem. Pharmacol., 67:41-51 (2004).

Shivakumar, et al., "The RASSF1A tumor suppressor blocks cell cycle progression and inhibits cyclin D1 accumulation", Mol. Cell. Biol., 22:4309-18 (2002).

Sinha, et al., "Mahanine inhibits growth and induces apoptosis in prostate cancer cells through the deactivation of Akt and activation of caspases", The Prostate., 66:1257-65 (2006).

Song, et al., "The tumour suppressor RASSFIA regulates mitosis by inhibiting the APC-Cdc20 Complex", Nat. Cell Bio., 6(2):129-137 (2004).

Tombal, "Hormone therapy for prostate cancer: What have we done with Charles Huggins\ legacy", Eu. Urology, 61:26-28 (2012).

Van der Weyden, et al., "The Ras-association domain family (RASSF) members and their role in human tumourigenesis", Biochem. Biophys. Ada., 1776:58-85 (2007).

Vos, et al., "A role for the RASSFIA tumor suppressor in the regulation of tubulin polymerization and genomic stability", Cancer Res., 64:4244-50 (2004).

Wang, et al., "Palladium-catalyzed homocoupling and cross-coupling reactions of aryl halides in poly(ethylene glycol", J. Org. Chem., 71:1284-87 (2006).

Illos, et al., "N-Danysyl-carbazoloquinone; a chemical and electrochemical fluorescent switch", Tetra Lttrs., 47:5543-6 (2006).

Ushiki, et al., "Fluorescence as a means for kinetic studies III bimolecular reaction of fluorescent reagent as quenching probes", Bull Chem. Soc. Jpn., 56:3181-2 (1983).

\* cited by examiner

A

B

FLUORESCENT REGULATORS OF RASSF1A EXPRESSION AND HUMAN CANCER CELL PROLIFERATION

RELATED APPLICATIONS

This application is a national phase filing under 35 U.S.C. § 371 of PCT/US2009/004681 filed under the Patent Cooperation Treaty on Aug. 14, 2009, which claims benefit of and priority to U.S. Provisional Application Ser. No. 61/189,059, entitled "FLUORESCENT REGULATORS OF RASSF1A EXPRESSION AND HUMAN CANCER CELL PROLIFERATION," filed Aug. 15, 2008, the contents of each being incorporated by reference in their entirety.

BACKGROUND OF THE INVENTION

The incidence of prostate cancer has increased 142% in recent years. According to the American Cancer Society, approximately 180,000 men will be diagnosed with prostate cancer each year (Landis, S H et al. CA Cancer J Clin (1999) 49: 8-31). Prostatic carcinoma is most invasive and the second leading cause of cancer death in men in USA (Boring, C C et al. CA Cancer J Clin (1993) 43: 7-26). In the early stage of prostate cancer, the growth of prostatic carcinoma cells is androgen-dependent and can be effectively treated by hormone ablation either using surgical or pharmacological methods (Huggins, C et al. Arch Surg (1941) 43: 209-223). However, hormone ablation therapy only causes a temporary regression of prostate tumors and invariably tumor become androgen-independent in 6-18 months (Pfeifer G P et al. Biol Chem (2002) 383: 907-14; Isaacs, J T Vitam Horm (1994) 49: 433-502). Therefore, androgen blockade is not the answer for treating prostate cancer.

SUMMARY OF THE INVENTION

In one aspect, the invention provides methods for the treatment of cancer in a subject, methods of suppressing the growth of a cell and methods of determining if one or more cells from a subject are cancer cells.

In one aspect the invention provides a dansyl-carbazole compound having the formula:

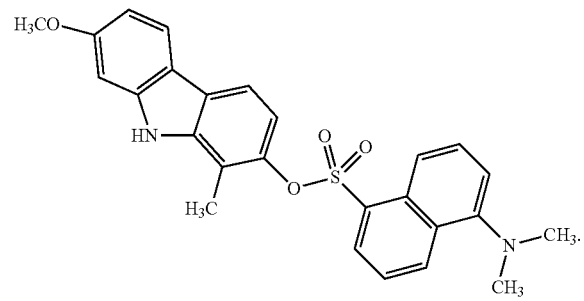 [SMILES: COc1ccc2c(c1)[nH]c1c(C)c(OS(=O)(=O)c3cccc4c(N(C)C)cccc34)ccc12]

In one aspect the invention provides methods for treating a cancer in a subject, the method comprising administering to a subject in need of such treatment a therapeutically effective amount of a composition comprising the dansyl-carbazole KED-4-69 to treat the cancer in the subject. In one aspect the invention provides uses of dansyl-carbazole KED-4-69 for treatment of a subject having cancer comprising administering to a subject in need of such treatment a therapeutically effective amount of a composition comprising the dansyl-carbazole KED-4-69 to treat the cancer in the subject. In one aspect the invention provides uses of the dansyl-carbazole KED-4-69 in the preparation of a medicament for treatment of a subject having cancer comprising administering to a subject in need of such treatment a therapeutically effective amount of a composition comprising the dansyl-carbazole KED-4-69 to treat the cancer in the subject. In some embodiments of the methods and uses provided herein the treatment suppresses further growth of the cancer. In some embodiments of the methods and uses provided herein the treatment results in regression of the cancer. In some embodiments of the methods and uses provided herein the cancer comprises cancer cells with decreased Ras-association domain family 1A (RASSF1A) expression. In some embodiments, the Ras-association domain family 1A (RASSF1A) expression is decreased by an increase in methylation of the promoter for RASSF1A. In some embodiments, the administration of the composition increases Ras-association domain family 1A (RASSF1A) expression. In some embodiments, the cancer is prostate cancer. In some embodiments, mahanine analogs or analogs of KED-4-69 are administered.

In one aspect the invention provides methods for suppressing the growth of a cell, the method comprising contacting the cell with a composition comprising the compound of claim 1 to suppress the growth of the cell. In some embodiments, the cell has decreased Ras-association domain family 1A (RASSF1A) expression. In some embodiments, the cell is a cancer cell. In some embodiments, the cancer cell is a prostate cancer cell. In some embodiments, the cell is in a subject. In some embodiments, the cell is contact with mahanine analogs or analogs of KED-4-69.

In one aspect the invention provides methods for reducing DNA methyltransferase activity in a cell, the method comprising contacting the cell with a composition comprising the dansyl-carbazole KED-4-69 to reduce DNA methyltransferase activity in the cell. In some embodiments, the DNA methyltransferase activity is reduced by reducing the activity of DNMT-3b. In some embodiments, the methyltransferase activity is reduced by sequestering DNMT-3b to the cytoplasm. In some embodiments, the cell is a cancer cell. In some embodiments, the cancer cell is a prostate cancer cell. In some embodiments, the cell is in a subject. In some embodiments, the cell is contact with mahanine analogs or analogs of KED-4-69.

In one aspect the invention provides methods for increasing Ras-association domain family 1A (RASSF1A) expression in a cell, the method comprising contacting the cell with a composition comprising the dansyl-carbazole KED-4-69 to increase RASSF1A expression in the cell. In some embodiments, the cell has decreased Ras-association domain family 1A (RASSF1A) expression. In some embodiments, the cell is a cancer cell. In some embodiments, the cancer cell is a prostate cancer cell. In some embodiments, the cell is contact with mahanine analogs or analogs of KED-4-69.

In one aspect the invention provides methods of identifying a cell in which Ras-association domain family 1A (RASSF1A) expression is decreased, the method comprising contacting the cell with a composition comprising the dansyl-carbazole KED-4-69, wherein if the compound is retained in the cell, the cell is identified as having decreased RASSF1A expression. In some embodiments, the cell is in a subject. In some embodiments, the cell is contact with mahanine analogs or analogs of KED-4-69.

In one aspect the invention provides methods of determining if one or more cells from a subject are cancer cells, the method comprising obtaining one or more cells from a subject, contacting the one or more cells with a composition comprising the dansyl-carbazole KED-4-69, measuring the fluorescence of the one or more cells, wherein if the fluorescence of the one or more cells is indicative of the presence of the dansyl-carbazole KED-4-69, the one or more cells is identified as being a cancer cell. In some embodiments, the fluorescence of the one or more cells is compared to a control cell. In some embodiments, the one or more cells is contact with mahanine analogs or analogs of KED-4-69.

In one aspect the invention provides a pharmaceutical composition comprising the dansyl-carbazole KED-4-69 and a pharmaceutically acceptable carrier. In some embodiments, the pharmaceutical composition further comprises one or more additional anti-cancer compounds.

In one aspect the invention provides a kit comprising a pharmaceutical composition comprising a therapeutically effective amount of the dansyl-carbazole KED-4-69, and instructions for preparation and/or administration of the pharmaceutical composition. In some embodiments, the kit further comprises a pharmaceutically acceptable carrier. In some embodiments, the kit further comprises one or more additional anti-cancer compounds.

In some aspects, the invention provides methods for the treatment of cancer in an individual. In some embodiments, the invention provides method for the treatment of prostate cancer in an individual. In some embodiments, the invention provides methods for the treatment of cancer in which Ras-association domain family 1A (RASSF1A) expression is decreased in some or all cancer cells. In some embodiments, the invention provides methods for the treatment of cancer in which DNA methyltransferase (DNMT) activity is increased in some or all cancer cells. In some embodiments, the methods of treatment comprise the administration of dansyl-carbazole KED-4-69.

In some embodiments, the invention provides methods for diagnosing cancer using dansyl-carbazole KED-4-69. In some embodiments, the invention provides methods of identifying a cell in which Ras-association domain family 1A (RASSF1A) is epigenetically silenced. In some embodiments, the methods of identifying a cell in which Ras-association domain family 1A (RASSF1A) comprise contacting a cell with dansyl-carbazole (KED-4-69).

The invention also encompasses the use of dansyl-carbazole KED-4-69 as a research tool and/or a research reagent.

Applicants synthesized a dansyl-carbazole compound KED-4-69 and demonstrated that the compound inhibits growth in PC3 prostate cancer cells in vitro. In addition, as described herein, the dansyl-carbazole compound induces the expression of RASSF1A in human prostate cancer cells. Furthermore, it is shown herein that treatment with the dansyl-carbazole compound represses cyclin D1 transcriptional activity in prostate cancer cells. The expression of RASSF1A is associated with a decrease in cyclin D1 activity.

According to one aspect of the invention a dansyl-carbazole compound having the formula:

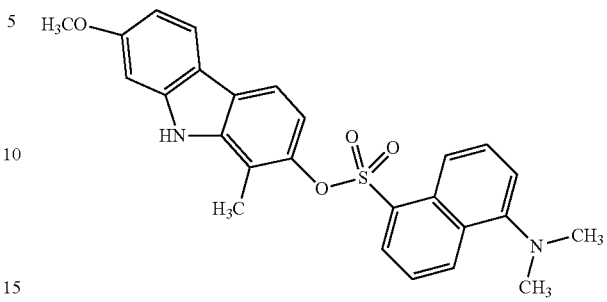

is provided.

According to another aspect of the invention, a method of inducing expression of an epigenetically silenced gene, Ras-association domain family 1A (RASSF1A) in cells is provided. The method comprises contacting the cells with the compound shown in FIG. 1A. In some embodiments, the cells are human cancer cells. In some of the preferred embodiments, the cancer cells are prostate cancer cells. The cells may be in an individual.

According to another aspect of the invention, a method of treating an individual for cancer in which Ras-association domain family 1A (RASSF1A) is epigenetically silenced is provided. The method comprises administering to the individual a therapeutically effective amount of the compound as shown in FIG. 1A that induces expression of RASSF1A in cancer cells or precancer cells in the individual, thereby limiting the extent to which a cancer in which RASSF1A is epigenetically silenced occurs in the individual or reversing (partially or completely) a cancer in which RASSF1A is epigenetically silenced in the individual. The cancer in which RASSF1A is epigenetically silenced may be prostate cancer, skin cancer, lung cancer, pancreatic cancer, colon cancer, breast cancer, ovarian cancer or another cancer.

According to another aspect of the invention, a method of treating prostate cancer in a man is provided. The method comprises administering to the man a therapeutically effective amount of the compound shown in FIG. 1A, whereby expression of epigenetically silenced RASSF1A is induced and prostate cancer occurs to a lesser extent than would be case in the absence of administration of the compound of shown in FIG. 1A. The compound may be administered by a parenteral route, such as a subcutaneous, intramuscular, intraorbital, intracapsular, intraspinal, intrasternal, or by an intravenous route. In some embodiments the compound is administered enterally, which includes oral administration, such as by oral gavage.

According to another aspect of the invention, a method of suppressing or inhibiting DNA methyltransferase (DNMT) activity in a cell is provided. The method comprises contacting the cell with the compound shown in FIG. 1A. In some embodiments, the DNMT activity is lowered by lowering the activity of DNMT-3b. In some embodiments, the cells are in an individual.

According to another aspect of the invention, a method of identifying a cell in which Ras-association domain family 1A (RASSF1A) is epigenetically silenced is provided. The method, comprises contacting the cell with the compound shown in FIG. 1A, wherein if the compound is retained in the cell, the cell is identified as being epigenetically silent for RASSF1A. In some embodiments, the cell is in a subject.

In one aspect, the invention provides a dansyl-carbazole compound having a structure:

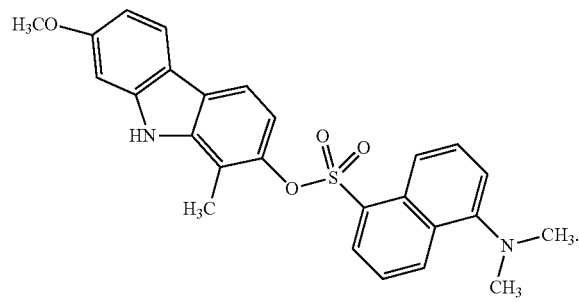 [SMILES: COc1ccc2c(c1)[nH]c1c(C)c(OS(=O)(=O)c3cccc4c(N(C)C)cccc34)ccc12]

In one aspect, the invention provides a method of inducing expression of an epigenetically silenced gene, Ras-association domain family 1A (RASSF1A) in cells, comprising contacting the cells with the dansyl-carbazole compound of FIG. 1A. In some embodiments, the cells are human cancer cells. In some embodiments, the human cancer cells are prostate cancer cells. In some embodiments, the cells are in an individual.

In one aspect, the invention provides a method of treating an individual for cancer in which Ras-association domain family 1A (RASSF1A) is epigenetically silenced, comprising administering to the individual a therapeutically effective amount of the compound of FIG. 1A that induces expression of RASSF1A in cancer cells or precancer cells in the individual, thereby limiting the extent to which a cancer in which RASSF1A is epigenetically silenced occurs in the individual or reversing (partially or completely) a cancer in which RASSF1A is epigenetically silenced in the individual. In some embodiments, the cancer is prostate cancer, skin cancer, lung cancer, pancreatic cancer, colon cancer, breast cancer, ovarian cancer or other cancer in which RASSF1A is epigenetically silenced.

In one aspect, the invention provides a method of treating prostate cancer in a man, comprising administering to the man a therapeutically effective amount of the compound of FIG. 1A, whereby expression of epigenetically silenced RASSF1A is induced and prostate cancer occurs to a lesser extent than would be case in the absence of administration of the compound of FIG. 1A. In some embodiments, the compound of FIG. 1A is administered by a parenteral route, such as a subcutaneous, intramuscular, intraorbital, intracapsular, intraspinal, intrasternal, or intravenous route.

In one aspect, the invention provides a method of suppressing or inhibiting DNA methyltransferase (DNMT) activity in a cell, comprising contacting the cell with the compound of FIG. 1A. In some embodiments, DNMT activity in a cell is lowered by lowering the activity of DNMT-3b. In some embodiments, the cells are in an individual.

In one aspect, the invention provides a method of identifying a cell in which Ras-association domain family 1A (RASSF1A) is epigenetically silenced, comprising contacting the cell with the compound of FIG. 1A, wherein if the compound is retained in the cell, the cell is identified as being epigenetically silent for RASSF1A. In some embodiments, the cell is in a subject.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including", "comprising", "having", "containing", "involving", and variations thereof herein, is meant to encompass the items listed thereafter and equivalents thereof as well as additional items.

BRIEF DESCRIPTION OF THE DRAWINGS

The figures are illustrative only and are not required for enablement of the invention disclosed herein.

DETAILED DESCRIPTION OF THE INVENTION

Figure 1:
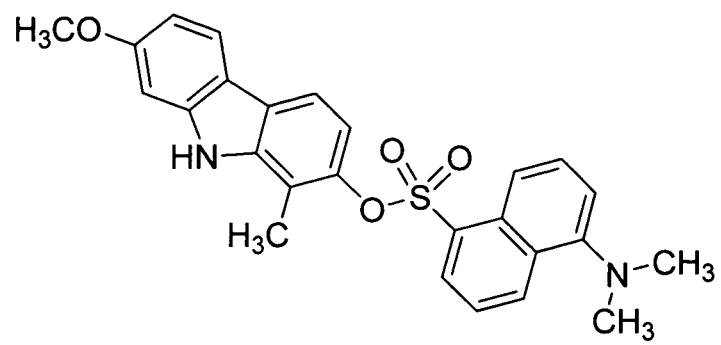
FIGS. 1A-B show the structure of a dansyl-carbazole of the invention (i.e., KED-4-69, compound 6a) (A) and mahanine (B).
Figure 1:
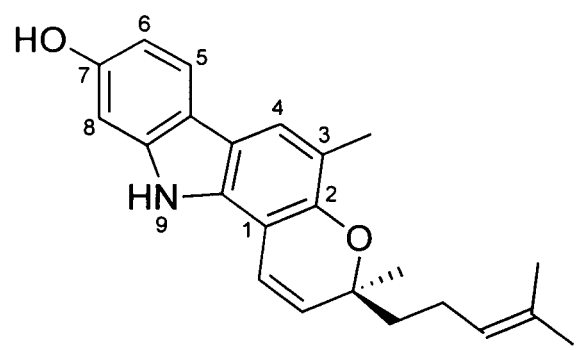

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

In one aspect, the invention provides methods for treating a cancer in a subject. In some embodiments, the method comprises administering to a subject in need of such treatment a therapeutically effective amount of a composition comprising a carbazole compound to treat the cancer in the subject. In some embodiments, the carbazole compound is the dansyl-carbazole compound of FIG. 1A (i.e., KED-4-69 or compound 6a). In some embodiments, the treatment suppresses further growth of the cancer and/or results in regression of the cancer. In some embodiments, the cancer comprises cancer cells with decreased Ras-association domain family 1A (RASSF1A) expression. In some embodiments, the Ras-association domain family 1A (RASSF1A) expression is decreased by an increase in methylation of the promoter for RASSF1A. In some embodiments, the administration of the composition increases Ras-association domain family 1A (RASSF1A) expression. In some embodiments, the cancer is prostate cancer.

In some aspects, the invention provides methods for the treatment of cancer in an individual. In some embodiments, the invention provides method for the treatment of prostate cancer in an individual. In some embodiments, the invention provides methods for the treatment of cancer in which Ras-association domain family 1A (RASSF1A) expression is suppressed in some or all cancer cells. In some embodiments, the invention provides methods for the treatment of cancer in which DNA methyltransferase (DNMT) activity is increased in some or all cancer cells. In some embodiments, the methods of treatment comprise the administration of dansyl-carbazole KED-4-69.

A commonly found aberration in human tumors is promoter methylation of the Ras-association domain family 1A (RASSF1A) gene (van der Weyden, L. et al. *Biochem. Biophys. Acta.* 2007, 1776, 58-85). Located on chromosome 3p21.3, the RASSF1 gene locus codes for seven different transcripts, with RASSF1A being one of two major isoforms found in normal cells. These Ras effector proteins share a conserved motif, the Ra1GDS/AF6 Ras association domain, and their effects on Ras-mediated proliferation and apoptosis have shown them to be tumor suppressors. The loss of RASSF1A protein expression which results from hypermethylation (epigenetic) silencing disrupts cell cycle control, induces genetic instability, enhances cell motility and provides for apoptotic resistance in cancer cells. The reversal of this tumorigenic phenotype, however, can be induced by ectopic expression of RASSF1A (van der Weyden, L. et al. *Biochem. Biophys. Acta.* 2007, 1776, 58-85; Donninger, H. et al. *J. of Cell Sci.* 2007, 120, 3163-3172).

The etiology of human prostatic carcinoma remains largely undefined. However, it is becoming clear that epigenetic inactivation of various tumor suppressor genes plays a pivotal role in the development of various cancers, including prostate cancer. One such tumor suppressor is the Ras-association domain family 1 (RASSF1) gene. Two major isoforms of RASSF1, A and C, are produced from the human RASSF1 gene on chromosome 3p21.3 (1, 2). A diacylglycerol-binding domain is present at the amino-terminus of RASSF1A. The carboxy-terminus of RASSF1A contains a Ras-association domain. The biological function of RASSF1A is largely unknown. RASSF1C is a smaller protein (50 amino acids) that lacks the amino-terminal C1 domain. RASSF1C is thought to play a role in RAS-mediated cellular activities (3). In prostate cancer, loss of function of classic tumor suppressor genes such as RB1 is not frequently found; however, the RASSF1A promoter region is methylated in 71% of primary prostate tumors. When considering only more aggressive prostate tumors (Gleason score 7-10), the incidence of RASSF1A methylation increases to nearly 85% (Li et al., Biochim. Biophys. Acta, 2004, 1704: 87-102). In contrast, RASSF1A promoter methylation is not found in primary normal prostate epithelial and stromal cells (Kuzmin et al., Cancer Res. 2002, 62: 3498-3502).

RASSF1A is probably the most frequently methylated gene described thus far in human cancers (4, 5). RASSF1A gene methylation has been reported in at least 37 tumor types. For example, methylation of RASSF1A is found in 80% of small cell lung cancers (2, 6), over 60% of breast tumors (2, 7, 8), 90% of liver cancers (9-11), 63% of pancreatic tumor (12), 40% of nonileal tumors (12), 69% of ileal tumors (12), 70% of primary nasopharyngeal cancers (13), 91% of primary renal cell carcinomas (14), 62% bladder tumor (15) and over 70% of prostate cancers (16-18).

Ectopic expression of RASSF1A in cancer cell lines that lack endogenous RASSF1A transcripts resulted in reduced growth of the cells in vitro and in nude mice, supporting a role for RASSF1A as a tumor suppressor gene (1, 2, 14, 16, 19-21). It has been demonstrated that the association of both RASSF1A and NORE1 (novel Ras effector 1) with the proapoptotic kinase, MST1 (mammalian sterile 20-like 1) leads to the induction of apoptosis (22). Other studies showed that RASSF1A is a microtubule-binding protein that can stabilize microtubules and that its over-expression causes metaphase arrest by interacting with the components of the anaphase promoting complex (23-26). It has also been shown that RASSF1A suppresses the c-Jun-NH2-kinase pathway resulting in the inhibition of cell cycle progression (30). Thus, RASSF1A plays a role in the regulation of the cell cycle.

RASSF1A KO-mice were viable and fertile but, as expected, were prone to spontaneous tumorigenesis (lymphoma, leukemia, lung adenoma, breast adenocarcinoma, rectal papiloma) in advanced age (18-20 months) (27). Shivakumar and associates have shown that the exogenous expression of RASSF1A induced cell cycle arrest in human lung cancer cells (H1299) at the G1 phase which was associated with the down regulation of cyclin D1 (28). RASSF1A also interacts with p120$^{E4F}$, a negative modulator of cyclin A expression (29).

The restoration of RASSF1A expression in tumor cell lines impairs their tumorigenicity (14, 16) and, therefore, restoring RASSF1A expression offers a method for cancer prevention and treatment.

As described herein, the compounds of the invention induce the expression of an epigenetically silenced tumor suppressor gene, RASSF1A, in human prostate cancer cells. In addition, the compounds of the invention have been shown to down-regulate cyclin D1. The repression of cyclin D1 transcription by the compounds of the invention via the RASSF1A pathway provides a new cancer treatment method.

Transcription of the cyclin D1 gene is induced via distinct DNA sequences in its promoter by diverse mitogenic and oncogenic signaling pathways including Ras, Src, Stat3, Stat5 and Erbb2 (37). Several transcription factors, such as CREB, AP-1, β-catenin/Tcf-1, have been shown to interact with the cyclin D1 promoter (35, 38). One or more of these signaling pathways and transcription factors are likely involved in the transcriptional regulation of cyclin D1 by RASSF1A. The activation of cyclin D1 gene transcription is dependent on the activation of Ras, Raf, mitogen activated protein kinase-kinases (MEK1 and MEK2), Akt and the sustained activation of extracellular signal regulates protein kinases (ERKs) (37). On the other hand, cyclin D1 degradation is mediated by phosphorylation-triggered ubiquitin-dependent proteolysis (39). Glycogen synthase kinase 3β (GSK-3β) catalyzes the phosphorylation of cyclin D1 on Thr286 and redirects the protein from the nucleus to the cytoplasm (39).

Overexpression of cyclin D1 is a common event in various forms of cancer, including prostate cancer (40-42). The overexpression of cyclin D1 leads to enhanced organ growth in mice (43). Transient transfection of hepatocytes with cyclin D1 leads to vigorous proliferation and more than 50% increase in liver mass within 6 days (44). Conversely, cyclin D1 knockout mice are smaller than wild-type mice and mice with the homozygous deletion of the p27 gene (which inhibits cyclin D1/Cdk4/6 complexes) show gigantism and enhanced organ size (45). Moreover, the expression of cyclin D1 modulates invasive ability by increasing matrix metalloproteinase (MMP-2 and MMP-9) activity and motility in glioma cells (46). Furthermore, over-expression of cyclin D1 is associated with metastatic prostate cancer to bone (47). These findings show that in addition to its well defined role in cell cycle progression, cyclin D1 plays an important role in the regulation of cell growth and metastasis.

In one aspect, the invention provides methods for treating a cancer in a subject. In one aspect, the invention provides methods for suppressing the growth of a cell, the method comprising contacting the cell with a composition comprising the compound of FIG. 1A (i.e., KED-4-69 or compound 6a) to suppress the growth of the cell. In some embodiments, the cell has decreased Ras-association domain family 1A (RASSF1A) expression.

In one aspect, the invention provides methods for reducing DNA methyltransferase activity in a cell, the method comprising contacting the cell with a composition comprising the compound of FIG. 1A (i.e., KED-4-69 or compound 6a) to reduce DNA methyltransferase activity in the cell. In some embodiments, DNA methyltransferase activity is reduced by reducing the activity of DNMT-3b. In some embodiments, DNA methyltransferase activity is reduced by sequestering DNMT-3b to the cytoplasm.

In one aspect, the invention provides methods for increasing Ras-association domain family 1A (RASSF1A) expression in a cell, the method comprising contacting the cell with a composition comprising the compound of FIG. 1A (i.e., KED-4-69 or compound 6a) to increase RASSF1A expression in the cell. In some embodiments, the cell has decreased Ras-association domain family 1A (RASSF1A) expression. In some embodiments, the cell is a cancer cell a prostate cancer cell and/or is in a subject.

It is shown herein that the compounds of the invention suppress the activity of DNMT, an event that can precipitate the restoration of RASSF1A expression and thereby act as a method of cancer therapy. It has been demonstrated that promoter hypermethylation is the major cause of RASSF1A gene silencing in variety of human cancers (2, 4-18). Methylation of the DNA in the cell is done by DNA methyltransferases (DNMTs). The cell contains three enzymatically active DNMT variants (DNMT-1, -3a and -3b), of which DNMT-3b is the only one found in the cytoplasm as well as the nucleus (Majumder, S. et al. *J. of Biol. Chem.* 2002, 277, 16048-16058). The compounds of the invention suppress methylation most likely through binding to DNMT-3b as shown by the localization of the fluorescent compound 6a. Upon contacting PC-3 cells with this compound, fluorescent images show that the compound is located solely in the cytoplasm of the PC-3 cells. These findings show that compound 6a interacts with DNMT-3b. Thus, the dansyl-carbazole compound has an isoform-specific mode of action. Because of the isoform-specific action of the dansyl-carbazole compound of the invention cytotoxicity, which is associated with nucleoside DNMT inhibitors, is likely avoided (Lyko, F. et al. *J. Natl. Cancer Inst.* 2005, 97, 1498-1506).

Figure 2:
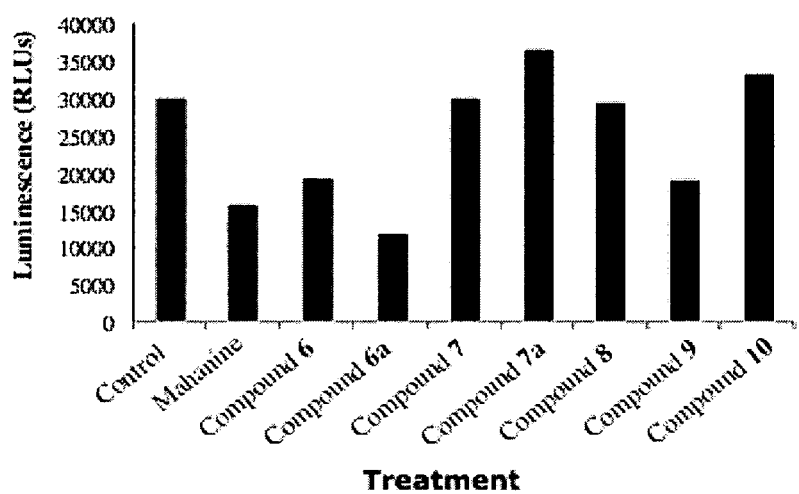
FIG. 2 shows that decreased DNA synthesis is observed in compounds treated with mahanine analogs, including the dansyl-carbazole compound KED-4-69 (i.e., compound 6a). PC-3 cells were plated in 96-well plates and treated with 5 μM of compound. After 24 hours, the cells were assayed for BrdU labeling using the Cell Proliferation ELISA BrdU kit from Roche; background BrdU incorporation levels (absent anti-BrdU-peroxidase solution) were subtracted and values were normalized to those of control untreated cells.

Applicants synthesized a number of mahanine analogs (See FIG. 5) and demonstrated that these compound inhibit the growth of PC3 prostate cancer cells (See e.g., FIG. 2). In addition, as described herein, these mahanine analogs induce the expression of RASSF1A in human prostate cancer cells, while suppressing DNMT activity (See e.g., FIG. 7). Furthermore, it is shown herein that treatment with the mahanine analogs also represses cyclin D1 transcriptional activity in prostate cancer cells (See e.g., FIG. 2). The expression of RASSF1A is associated with a decrease in cyclin D1 message and protein levels and G0/G1 cell cycle arrest in prostate cancer cells. That is, there is an inverse relationship between RASSF1A and cyclin D1 expression. RASSF1A represses cyclin D1 transcription by inhibiting its promoter activity and addition of RASSF1A siRNA prevents this inhibition.

The compounds of the invention are also referred to herein as mahanine analogs, as they are based on the same carbazole structure. The natural product mahanine is a potent growth inhibitor of androgen independent human prostate cancer cells (See e.g., PCT/US2007/02241 which is incorporated herein by reference in its entirety). An increase in RASSF1A mRNA level was observed in mahanine-treated PC-3 cells, as well as a decrease in the level of cyclin D1 mRNA. This is consistent with previous findings that increased RASSF1A expression down-regulates cyclin D1, resulting in inhibited cell growth (Shivakumar, L. et al. *Mol. Cell. Biol.* 2002, 22, 4309-4318). Applicants also previously demonstrated (33) that mahanine deactivated Akt in prostate cancer cells. Activated Akt deactivates GSK-3β by phosphorylation. Therefore, it is possible that in addition to the transcriptional repression of cyclin D1 by RASSF1A, the dansyl-carbazole compound also deactivates Akt, which would eventually activate GSK-3β to degrade cyclin D1.

The anti-proliferative activity of mahanine is associated with its inhibition of DNA methyltransferase (DNMT) activity in PC-3 cells. The RASSF1A promoter region is methylated in 71% of primary prostate tumors, with the instances increasing to 83% when considering only more aggressive tumors (those with a Gleason score of 7-10; Liu, L. et al. *Oncogene*. 2002, 21, 6835-6840). Presumably, inhibition of DNMT activity by mahanine prevents the hypermethylation and subsequent silencing of the RASSF1A gene. Such epigenetic regulation of RASSF1A and other hypermethylated genes has been observed previously in a variety of cell lines, including prostate cancer (Brueckner, B. et al. *Cancer Res*. 2005, 65, 6305-6311; Li, L. et al. *Biochem. Biophys. Acta*. 2004, 1704, 87-102; Beaulieu, N. et al. *J. Biol. Chem.* 2002, 31, 28-176-28181).

Just like mahanine, the compounds disclosed herein have the ability to suppress the growth of cancer cells, as evidenced by experiments with prostate cancer cells. One of the compounds disclosed herein, compound 6a, has a 5-fold increase in activity when compared to mahanine in the inhibition of growth of prostate cancer cells (See Table 1). In addition to inhibiting human prostate cell proliferation at a lower dose than mahanine compound 6a is less cytotoxic than mahanine. The compounds of the invention upregulate the protein suppressor protein RASSF1A, down-regulate cyclin D1 and suppress DNMT activity, with compound 6a showing the strongest effect.

In one aspect, the invention provides methods of identifying a cell in which Ras-association domain family 1A (RASSF1A) expression is decreased, the method comprising contacting the cell with a composition comprising a fluorescent mahanine analog, wherein if the compound is retained in the cell, the cell is identified as having decreased RASSF1A expression. In some embodiments, the fluorescent mahanine analog is the compound of FIG. 1A (i.e., KED-4-69 or compound 6a). In some embodiments, the cell is in a subject.

In one aspect the invention provides a method of determining if one or more cells from a subject are cancer cells, the method comprising obtaining one or more cells from a subject, contacting the one or more cells with a composition comprising a fluorescent mahanine analog, measuring the fluorescence of the one or more cells, wherein if the fluorescence of the one or more cells is indicative of the presence of the fluorescent mahanine analog, the one or more cells is identified as being a cancer cell. In some embodiments, the fluorescent mahanine analog is the compound of FIG. 1A (i.e., KED-4-69 or compound 6a). In some embodiments, the fluorescence is compared to a control cell. A control cell can both be a wild type control cell (i.e., a negative control which is not expected to retain the fluorescent mahanine analog) or a cancer cell with decreased RASSF1A expression (i.e., a positive control, which will provide a fluorescence indicative of the presence of the fluorescent mahanine analog).

The authors have shown that mahanine analogs can bind DNMT3b and can sequester DNMT3b in the cytoplasm. Thus, fluorescent mahanine analogs, such as compound 6a, allow for methods of monitoring the movement of DNMT3b within the cell. In addition, the fluorescent mahanine analogs allow for the identification of cells in which DNMT, as evidenced by DNMT3b, is an important factor in the methylation of RASFF1. Thus, the fluorescent mahanine analogs of the invention allow for the identification of cells, such as prostate cancer cells, in which RASSF1 is downregulated. The fluorescent mahanine analogs of the invention therefore provide a diagnostic tool for in vitro and in vivo determination of the "cancer" status of a cell (e.g., if the cell has a downregulated RASSF1 the cell is likely to be a cancer cell). In addition, the fluorescent mahanine analogs of the invention are useful in a variety of assays, such as in drug discovery, where it is of importance to determine RASSF1 and/or DNMT3b activity and DNMT3b localization.

In any one or more of the embodiments described herein the method comprises administering to a subject, or contacting a cell with, a composition comprising a carbazole compound. In some embodiments, the carbazole compound is a carbazole compound comprising a heteroaryl group. In some embodiments, the carbazole compound is a dansyl-carbazole. In some embodiments, the dansyl-carbazole compound has the following structure:

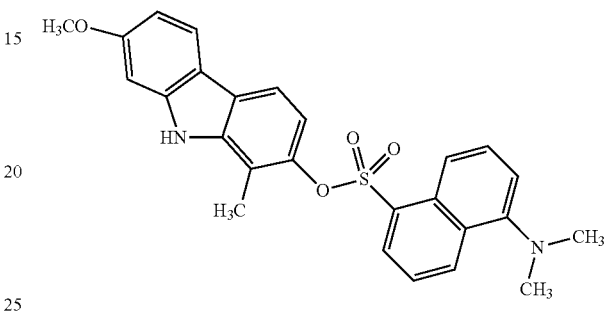

The above depicted dansyl-carbazole compound will also be referred to herein as "KED-4-69", "compound 6a", "the compound of FIG. 1A" or "the compound shown in FIG. 1A".

Carbazole compounds are known in the art and are defined as an aromatic heterocyclic organic compound comprising a tricyclic structure consisting of two-six membered benzene rings fused on either side of a five-membered nitrogen-containing ring. In some embodiments, the carbazole compound is mahanine (FIG. 1B), compound 6a (FIG. 1A) compound 6, compound 7, compound 7a, compound 8, compound 9 or compound 10 (See FIG. 5 and FIG. 6). The compounds disclosed herein will also be referred to as mahanine analogs or the compounds of the invention.

In some embodiments, the carbazole compound is a carbazole compound comprising an aryl group substituent. In some embodiments, the compound comprises at least one benzyl group substituent, wherein the benzyl group comprises a phenyl ring. In some cases, the phenyl ring may be optionally substituted with at least one OH, $NH_2$, $NHR_9$, $OCH_3$, or alkyl group, wherein $R_9$ is H, alkyl, C=O, or S=O. In some embodiments, the carbazole compound is compound 6a (See FIG. 5).

In some embodiments, the carbazole compound is a carbazole compound comprising a heteroaryl group substituent. A heteroaryl group comprises a non-carbon molecule (the heterogroup) coupled to an aryl group. In some embodiments, the heterogroup is $SO_2$, SO, CO, NH or $PO_3$. In some embodiments, the aryl group comprises one or more phenyl rings. In some embodiments, the aryl group is substituted with at least one OH, $NH_2$, $NR_1R_2$, $NHR_1$, $OCH_3$, $OCHR_1R_2$, $OCH_2R_1$, $OCR_1R_2R_3$, C=O, or S=O, wherein $R_1$, $R_2$ and $R_3$ are alkyl groups. In some embodiments, the heteroaryl group is a dansyl group. In some embodiments, the heteroaryl group is a fluorescent group. In some embodiments, the dansyl-carbazole compound is the compound of FIG. 1A (i.e., KED-4-69 or compound 6a).

In some embodiments, the compounds described herein may be "optionally substituted," that is, the compounds may be substituted or unsubstituted. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The invention also embraces KED-4-69 analogs. KED-4-69 analogs are chemically modified versions of KED-4-69. In some embodiments, the KED-4-69 analogs have one or more KED-4-69 activities (as described herein), e.g., anti-cancer activity. The one or more activities are preferably present in the KED-4-69 analogs in significant amounts, e.g., at greater than 10%, 20%, 30%, 40%, 50%, 60%, 70%, 80%, or 90% of the activity of KED-4-69, respectively. More preferably, the one or more activities are preferably present in the KED-4-69 analogs at greater than 100%, 110%, 120%, 130%, 140%, 150%, 160%, 170%, 180%, 190%, 200%, or more, of the activity of KED-4-69. The KED-4-69 analogs may not have all of the activities of KED-4-69. However, non-active KED-4-69 analogs, having none of the activities of KED-4-69 in significant amounts, are not useful in the methods of the invention.

The invention also embraces prodrugs of KED-4-69, KED-4-69 analogs and the other mahanine analogs disclosed herein. Prodrugs of KED-4-69, KED-4-69 analogs and mahanine analogs are modified versions of KED-4-69, KED-4-69 analogs and mahanine analogs that may have improved stability and/or handling properties compared to the unmodified version of KED-4-69, KED-4-69 analogs and mahanine analogs. Prodrugs of KED-4-69, KED-4-69 analogs and mahanine analogs are metabolized in vivo to result in KED-4-69, KED-4-69 analogs and mahanine analogs, respectively.

KED-4-69, analogs of KED-4-69, mahanine analogs and prodrugs of KED-4-69, prodrugs of analogs of KED-4-69 and prodrugs of mahanine analogs are also referred to herein as the compounds of the invention.

It should be appreciated that whenever the invention refers to methods of administration of KED-4-69, analogs of KED-4-69 or mahanine analogs, or methods of contacting a cell with KED-4-69, analogs of KED-4-69 or mahanine analogs, the invention also encompasses the administration of, or contacting of cells with, prodrugs of KED-4-69, prodrugs of analogs of KED-4-69 or prodrugs of mahanine analogs.

The invention also embraces the administration of prodrugs of KED-4-69, prodrugs of KED-4-69 analogs and prodrugs of mahanine analogs. The term "prodrug" as used herein refers to any compound that when administered to a biological system generates a biologically active compound (i.e., KED-4-69, KED-4-69 analog or mahanine analog) as a result of spontaneous chemical reaction(s), enzyme catalyzed chemical reaction(s), and/or metabolic chemical reaction(s), or a combination of two or more of these reactions. Standard prodrugs are formed using groups attached to functionality, e.g. HO—, HS—, HOOC—, $R_2N$—, associated with the drug, that cleave in vivo. Standard prodrugs include, but are not limited to, carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated are exemplary, not exhaustive, and one skilled in the art could prepare other known varieties of prodrugs. Prodrugs can undergo some form of a chemical transformation to produce the compound that is biologically active or is a precursor of the biologically active compound. In some cases, the prodrug is biologically active, usually less than the drug itself, and serves to improve drug efficacy or safety through improved oral bioavailability, pharmacodynamic half-life, etc. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Prodrugs are described, for example, in The Organic Chemistry of Drug Design and Drug Action, by Richard B. Silverman, Academic Press, San Diego, 1992. Chapter 8: "Prodrugs and Drug Delivery Systems" pp. 352-401; Design of Prodrugs, edited by H. Bundgaard, Elsevier Science, Amsterdam, 1985; Design of Biopharmaceutical Properties through Prodrugs and Analogs, Ed. by E. B. Roche, American Pharmaceutical Association, Washington, 1977; and Drug Delivery Systems, ed. by R. L. Juliano, Oxford Univ. Press, Oxford, 1980.

The compounds of the inventions are administered in effective amounts. An effective amount is a dosage of the compound sufficient to provide a medically desirable result. An effective amount means that amount necessary to delay the onset of, inhibit the progression of, or halt altogether the onset or progression of the particular condition or disease being treated. In the treatment of cancer, for example, in general, an effective amount will be, for example, that amount necessary to inhibit cancer cell replication, reduce cancer cell load, or reduce one or more signs or symptoms of the cancer. When administered to a subject, effective amounts will depend, of course, on the particular cancer being treated; the severity of the cancer; individual patient parameters including age, physical condition, size and weight, concurrent treatment, frequency of treatment, and the mode of administration. These factors are well known to those of ordinary skill in the art and can be addressed with no more than routine experimentation. In some embodiments, it is preferred to use the highest safe dose according to sound medical judgment.

In one aspect, the invention provides methods for the treatment of cancer in a subject. A "subject", as used herein, is a human or other vertebrate mammal including, but not limited to, mouse, rat, dog, cat, horse, cow, pig, sheep, goat, or non-human primate. The terms "subject" and "individual" as used herein can be used interchangeably. In some embodiments, the subject is man.

A "subject in need of treatment", as used herein, means a subject that is identified as being in need of treatment. For instance, a subject in need of cancer treatment is a subject identified as having cancer or being at risk for developing cancer. A subject may be diagnosed as being in need of treatment by a healthcare professional and/or by performing one or more diagnostic assays. For instance, a subject in need of cancer treatment may be a subject diagnosed with cancer or being at risk of cancer by a healthcare professional. Diagnostic assays to evaluate if a subject has a cancer or is at risk for developing cancer are known in the art.

As used herein, "treating a cancer" includes, but is not limited to, preventing or reducing the development of a cancer, reducing the symptoms of cancer, suppressing or inhibiting the growth of an established cancer, preventing metastasis and/or invasion of an existing cancer, promoting or inducing regression of the cancer, inhibiting or suppressing the proliferation of cancerous cells, reducing angiogenesis or increasing the amount of apoptotic cancer cells. In some embodiments, the compounds of the invention are administered to a subject at risk of developing a cancer for the purpose of reducing the risk of developing the cancer.

In some embodiments, the invention provides methods for treating a specific cancer. In some embodiments, the invention provides methods for treating prostate cancer. In some embodiments, the invention provides methods for treating a cancer comprising cancer cells with decreased RASSF1A expression. The cancer can consist exclusively of cells with decreased RASSF1A expression or the cancer may include a subpopulation of cells with decreased RASSF1A expression. The term "decreased RASSF1A expression" as used herein refers to cells that have decreased levels of RASSF1A expression, when compared to wild-type (i.e., non-cancer) cells. Assays that can detect the level or activation status of RASSF1A expression are known in the art and include western blots and protein array analysis. Decreased levels, as compared to wild-type, includes 1% or less, 5% or less, 10% or less, 20% or less, 50% or less, 100% or less RASSF1A when compared wild-type.

In some embodiments, the compounds of the invention can be used in therapeutically effective amounts. The term "therapeutically effective amount" or "effective amount", which can be used interchangeably, refers to the amount necessary or sufficient to realize a desired therapeutic effect, e.g., shrinkage of a tumor, inhibition or suppression of cell proliferation. An effective amount typically will vary from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

Also the subject of this invention are compositions, such as pharmaceutical compositions or formulations which comprise (1) at least the compound presented herein and (2) an appropriate (pharmaceutically useful) carrier. Actual dosage levels of active ingredients in the pharmaceutical compositions of the invention can be varied to obtain an amount of the active compound that is effective to achieve the desired therapeutic response for a particular patient, compositions, and mode of administration. The selected dosage level depends upon the activity of the particular compound, the route of administration, the severity of the condition being treated, the condition, and prior medical history of the patient being treated. However, it is within the skill of one in the art to start doses of the compound at levels lower than required to achieve the desired therapeutic effort and to gradually increase the dosage until the desired effect is achieved.

In some embodiments, KED-4-69 can be administered combined with other therapeutic agents. KED-4-69 and other therapeutic agent may be administered simultaneously or sequentially. When the other therapeutic agents are administered simultaneously they can be administered in the same or separate formulations, but are administered at the same time. The other therapeutic agents are administered sequentially with one another and with KED-4-69, when the administration of the other therapeutic agents and the KED-4-69 is temporally separated. The separation in time between the administration of these compounds may be a matter of minutes or it may be longer.

In some embodiments, the other therapeutic agent is an anti-cancer compound. As used herein, an "anti-cancer compound" refers to an agent which is administered to a subject for the purpose of treating a cancer. Anti-cancer compounds include, but are not limited to anti-proliferative compounds, anti-neoplastic compounds, anti-cancer supplementary potentiating agents and radioactive agents. One of ordinary skill in the art is familiar with a variety of anti-cancer agents, or can find those agents in the routine art, which are used in the medical arts to treat cancer.

In some embodiments, compounds of the invention are administered in conjunction with an anti-cancer therapy. Anti-cancer therapies include, but are not limited to, the administration of anti-cancer compounds, radiation and surgical procedures.

Compound and pharmaceutical compositions of the invention can be administered to a subject by any suitable route. For example, compositions can be administered orally, including sublingually, rectally, parenterally, intracisternally, intravaginally, intraperitoneally, topically and transdermally (as by powders, ointments, or drops), bucally, or nasally. The term "parenteral" administration as used herein refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation also is contemplated, including, for example, embedding a composition of the invention in the body such as, for example, in the brain, in the abdominal cavity, under the splenic capsule, brain, or in the cornea.

Compound of the present invention also can be administered in the form of liposomes. As is known in the art, liposomes generally are derived from phospholipids or other lipid substances. Liposomes are formed by mono- or multilamellar hydrated liquid crystals that are dispersed in an aqueous medium. Any nontoxic, physiologically acceptable, and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p. 33, et seq.

Dosage forms for topical administration of a compound of this invention include powders, sprays, ointments, and inhalants as described herein. The active compound is mixed under sterile conditions with a pharmaceutically acceptable carrier and any needed preservatives, buffers, or propellants which may be required. Ophthalmic formulations, eye ointments, powders, and solutions also are contemplated as being within the scope of this invention.

Pharmaceutical compositions of the invention for parenteral injection comprise pharmaceutically acceptable sterile aqueous or non-aqueous solutions, dispersions, suspensions, or emulsions, as well as sterile powders for reconstitution into sterile injectable solutions or dispersions just prior to use. Examples of suitable aqueous and non-aqueous carriers, diluents, solvents, or vehicles include water ethanol, polyols (such as, glycerol, propylene glycol, polyethylene glycol, and the like), and suitable mixtures thereof, vegetable oils (such, as olive oil), and injectable organic esters such as ethyl oleate. Proper fluidity can be maintained, for example, by the use of coating materials such as lecithin, by the maintenance of the required particle size in the case of dispersions, and by the use of surfactants.

Compositions also can contain adjuvants such as preservatives, wetting agents, emulsifying agents, and dispersing agents. Prevention of the action of microorganisms can be ensured by the inclusion of various antibacterial and antifungal agents, for example, paraben, chlorobutanol, phenol sorbic acid, and the like. It also may be desirable to include isotonic agents such as sugars, sodium chloride, and the like. Prolonged absorption of the injectable pharmaceutical form can be brought about by the inclusion of agents which delay absorption, such as aluminum monostearate and gelatin.

In some cases, in order to prolong the effect of the drug, it is desirable to slow the absorption of the drug from subcutaneous or intramuscular injection. This result can be accomplished by the use of a liquid suspension of crystalline or amorphous materials with poor water solubility. The rate of absorption of the drug then depends upon its rate of dissolution which, in turn, may depend upon crystal size and crystalline form. Alternatively, delayed absorption of a parenterally administered drug from is accomplished by dissolving or suspending the drug in an oil vehicle.

Injectable depot forms are made by forming microencapsule matrices of the drug in biodegradable polymers such a polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations also are prepared by entrapping the drug in liposomes or microemulsions which are compatible with body tissue.

The injectable formulations can be sterilized, for example, by filtration through a bacterial- or viral-retaining filter, or by incorporating sterilizing agents in the form of sterile solid compositions which can be dissolved or dispersed in sterile water or other sterile injectable medium just prior to use.

The invention provides methods for oral administration of a pharmaceutical composition of the invention. Oral solid dosage forms are described generally in Remington's Pharmaceutical Sciences, 18th Ed., 1990 (Mack Publishing Co. Easton Pa. 18042) at Chapter 89. Solid dosage forms for oral administration include capsules, tablets, pills, powders, troches or lozenges, cachets, pellets, and granules. Also, liposomal or proteinoid encapsulation can be used to formulate the present compositions (as, for example, proteinoid microspheres reported in U.S. Pat. No. 4,925,673). Liposomal encapsulation may include liposomes that are derivatized with various polymers (e.g., U.S. Pat. No. 5,013,556). In general, the formulation includes a compound of the invention and inert ingredients which protect against degradation in the stomach and which permit release of the biologically active material in the intestine.

In such solid dosage forms, the active compound is mixed with, or chemically modified to include, a least one inert, pharmaceutically acceptable excipient or carrier. The excipient or carrier preferably permits (a) inhibition of proteolysis, and (b) uptake into the blood stream from the stomach or intestine. In a most preferred embodiment, the excipient or carrier increases uptake of the compound, overall stability of the compound and/or circulation time of the compound in the body. Excipients and carriers include, for example, sodium citrate or dicalcium phosphate and/or (a) fillers or extenders such as starches, lactose, sucrose, glucose, cellulose, modified dextrans, mannitol, and silicic acid, as well as inorganic salts such as calcium triphosphate, magnesium carbonate and sodium chloride, and commercially available diluents such as FAST-FLO®, EMDEX®, STA-RX 1500®, EMCOMPRESS® and AVICEL®, (b) binders such as, for example, methylcellulose ethylcellulose, hydroxypropyhnethyl cellulose, carboxymethylcellulose, gums (e.g., alginates, acacia), gelatin, polyvinylpyrrolidone, and sucrose, (c) humectants, such as glycerol, (d) disintegrating agents, such as agar-agar, calcium carbonate, potato or tapioca starch, alginic acid, certain silicates, sodium carbonate, starch including the to commercial disintegrant based on starch, EXPLOTAB®, sodium starch glycolate, AMBERLITE®, sodium carboxymethylcellulose, ultramylopectin, gelatin, orange peel, carboxymethyl cellulose, natural sponge, bentonite, insoluble cationic exchange resins, and powdered gums such as agar, karaya or tragacanth; (e) solution retarding agents such a paraffin, (f) absorption accelerators, such as quaternary ammonium compounds and fatty acids including oleic acid, linoleic acid, and linolenic acid (g) wetting agents, such as, for example, cetyl alcohol and glycerol monosterate, anionic detergent surfactants including sodium lauryl sulfate, dioctyl sodium sulfosuccinate, and dioctyl sodium sulfonate, cationic detergents, such as benzalkonium chloride or benzethonium chloride, nonionic detergents including lauromacrogol 400, polyoxyl 40 stearate, polyoxyethylene hydrogenated castor oil 10, 50 and 60, glycerol monostearate, polysorbate 40, 60, 65, and 80, sucrose fatty acid ester, methyl cellulose and carboxymethyl cellulose; (h) absorbents, such as kaolin and bentonite clay, (i) lubricants, such as talc, calcium sterate, magnesium stearate, solid polyethylene glycols, sodium lauryl sulfate, polytetrafluoroethylene (PTFE), liquid paraffin, vegetable oils, waxes, CARBOWAX® 4000, CARBOWAX® 6000, magnesium lauryl sulfate, and mixtures thereof; (j) glidants that improve the flow properties of the drug during formulation and aid rearrangement during compression that include starch, talc, pyrogenic silica, and hydrated silicoaluminate. In the case of capsules, tablets, and pills, the dosage form also can comprise buffering agents.

Solid compositions of a similar type also can be employed as fillers in soft and hard-filled gelatin capsules, using such excipients as lactose or milk sugar, as well as high molecular weight polyethylene glycols and the like.

The solid dosage forms of tablets, dragees, capsules, pills, and granules can be prepared with coatings and shells, such as enteric coatings and other coatings well known in the pharmaceutical formulating art. They optionally can contain opacifying agents and also can be of a composition that they release the active ingredients(s) only, or preferentially, in a part of the intestinal tract, optionally, in a delayed manner. Exemplary materials include polymers having pH sensitive solubility, such as the materials available as EUDRAGIT® Examples of embedding compositions which can be used include polymeric substances and waxes.

The active compounds also can be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms can contain inert diluents commonly used in the art, such as, for example, water or other solvents, solubilizing agents and emulsifiers, such as ethyl alcohol, isopropyl alcohol ethyl carbonate ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydroflirfuryl alcohol, polyethylene glycols, fatty acid esters of sorbitan, and mixtures thereof.

Besides inert diluents, the oral compositions also can include adjuvants, such as wetting agents, emulsifying and suspending agents, sweetening, coloring, flavoring, and perfuming agents. Oral compositions can be formulated and further contain an edible product, such as a beverage. Oral composition can also be administered by oral gavage.

Suspensions, in addition to the active compounds, can contain suspending agents such as, for example ethoxylated isostearyl alcohols, polyoxyethylene sorbitol and sorbitan esters, microcrystalline cellulose, aluminum metahydroxide, bentonite, agar-agar, tragacanth, and mixtures thereof.

Also contemplated herein is pulmonary delivery of the compounds of the invention. The compound is delivered to the lungs of a mammal while inhaling, thereby promoting the traversal of the lung epithelial lining to the blood stream. See, Adjei et al., Pharmaceutical Research 7:565-569 (1990); Adjei et al., International Journal of Pharmaceutics 63:135-144 (1990) (leuprolide acetate); Braquet et al., Journal of Cardiovascular Pharmacology 13 (suppl.5): s.143-146 (1989)(endothelin-1); Hubbard et al., Annals of Internal Medicine 3:206-212 (1989)($\alpha$1-antitrypsin); Smith et al., J. Clin. Invest. 84:1145-1146 (1989) ($\alpha$1-proteinase); Oswein et al., "Aerosolization of Proteins," Proceedings of Symposium on Respiratory Drug Delivery II, Keystone, Colo., March, 1990 (recombinant human growth hormone); Debs et al., The Journal of Immunology 140:3482-3488 (1988) (interferon-$\gamma$ and tumor necrosis factor $\alpha$) and Platz et al., U.S. Pat. No. 5,284,656 (granulocyte colony stimulating factor).

Contemplated for use in the practice of this invention are a wide range of mechanical devices designed for pulmonary delivery of therapeutic products, including, but not limited to, nebulizers, metered dose inhalers, and powder inhalers, all of which are familiar to those skilled in the art.

Some specific examples of commercially available devices suitable for the practice of the invention are the ULTRAVENT® nebulizer, manufactured by Mallinckrodt, Inc., St. Louis, Mo.; the ACORN II® nebulizer, manufactured by Marquest Medical Products, Englewood, Colo.; the VENTOL® metered dose inhaler, manufactured by Glaxo Inc., Research Triangle Park, N.C.; and the SPINHALER® powder inhaler, manufactured by Fisons Corp., Bedford, Mass.

All such devices require the use of formulations suitable for the dispensing of a compound of the invention. Typically, each formulation is specific to the type of device employed and can involve the use of an appropriate propellant material, in addition to diluents, adjuvants, and/or carriers useful in therapy.

The composition is prepared in particulate form, preferably with an average particle size of less than 10 μm, and most preferably 0.5 to 5 μm, for most effective delivery to the distal lung.

Carriers include carbohydrates such as trehalose, mannitol, xylitol, sucrose, lactose, and sorbitol. Other ingredients for use in formulations may include lipids, such as DPPC, DOPE, DSPC and DOPC, natural or synthetic surfactants, polyethylene glycol (even apart from its use in derivatizing the inhibitor itself), dextrans, such as cyclodextran, bile salts, and other related enhancers, cellulose and cellulose derivatives, and amino acids.

Also, the use of liposomes, microcapsules or microspheres, inclusion complexes, or other types of carriers is contemplated.

Formulations suitable for use with a nebulizer, either jet or ultrasonic, typically comprise a compound of the invention dissolved in water at a concentration of about 0.1 to 25 mg of biologically active protein per mL of solution. The formulation also can include a buffer and a simple sugar (e.g., for protein stabilization and regulation of osmotic pressure). The nebulizer formulation also can contain a surfactant to reduce or prevent surface-induced aggregation of the inhibitor composition caused by atomization of the solution in forming the aerosol.

Formulations for use with a metered-dose inhaler device generally comprise a finely divided powder containing the inhibitor compound suspended in a propellant with the aid of a surfactant. The propellant can be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid also can be useful as a surfactant.

Formulations for dispensing from a powder inhaler device comprise a finely divided dry powder containing the inhibitor and also can include a bulking agent, such as lactose, sorbitol, sucrose, mannitol, trehalose, or xylitol, in amounts which facilitate dispersal of the powder from the device, e.g., 50 to 90% by weight of the formulation.

Nasal delivery of the compounds and composition of the invention also is contemplated. Nasal delivery allows the passage of the compound or composition to the blood stream directly after administering the therapeutic product to the nose, without the necessity for deposition of the product in the lung. Formulations for nasal delivery include those with dextran or cyclodextran. Delivery via transport across other mucous membranes also is contemplated.

Compositions for rectal or vaginal administration are preferably suppositories which can be prepared by mixing the compounds of the invention with suitable nonirritating excipients or carriers, such as cocoa butter, polyethylene glycol, or suppository wax, which are solid at room temperature, but liquid at body temperature, and therefore melt in the rectum or vaginal cavity and release the active compound.

In order to facilitate delivery of compounds across cell and/or nuclear membranes, compositions of relatively high hydrophobicity are preferred. Compounds can be modified in a manner which increases hydrophobicity, or the compounds can be encapsulated in hydrophobic carriers or solutions which result in increased hydrophobicity.

In one aspect, the invention provides kits comprising a pharmaceutical composition comprising one or more compounds of the invention and instructions for administration of the pharmaceutical composition. In some aspects of the invention, the kit can include a pharmaceutical preparation vial, a pharmaceutical preparation diluent vial, and the compound of the invention. The diluent vial contains a diluent such as physiological saline for diluting what could be a concentrated solution or lyophilized powder of the compound of the invention. In some embodiments, the instructions include instructions for mixing a particular amount of the diluent with a particular amount of the concentrated pharmaceutical preparation, whereby a final formulation for injection or infusion is prepared. In some embodiments, the instructions include instructions for use in a syringe or other administration device. In some embodiments, the instructions include instructions for treating a patient with an effective amount of the compounds of the invention. It also will be understood that the containers containing the preparations, whether the container is a bottle, a vial with a septum, an ampoule with a septum, an infusion bag, and the like, can contain indicia such as conventional markings which change color when the preparation has been autoclaved or otherwise sterilized.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove.

EXAMPLES

Materials and Methods 1: Chemistry.

All reagents and solvents were purchased from commercial suppliers and used as received. Melting points were determined in open capillary tubes on an Electrothermal melting point apparatus and are uncorrected. $^1$H and $^{13}$C NMR spectra were measured at 22.5° C. on compounds in solution in CDCl$_3$ or DMSO-d$_6$ on a Varian 400 Mz spectrometer (Palo Alto, Calif.). Mass spectra were obtained on a Finnegan LcQ Classic (Thermo, Waltham, Mass.). Elemental analyses were preformed by Atlantic Microlabs (Norcross, Ga.), and micro analytical data were within ±0.4% of the calculated values unless specified.

Figure 5:
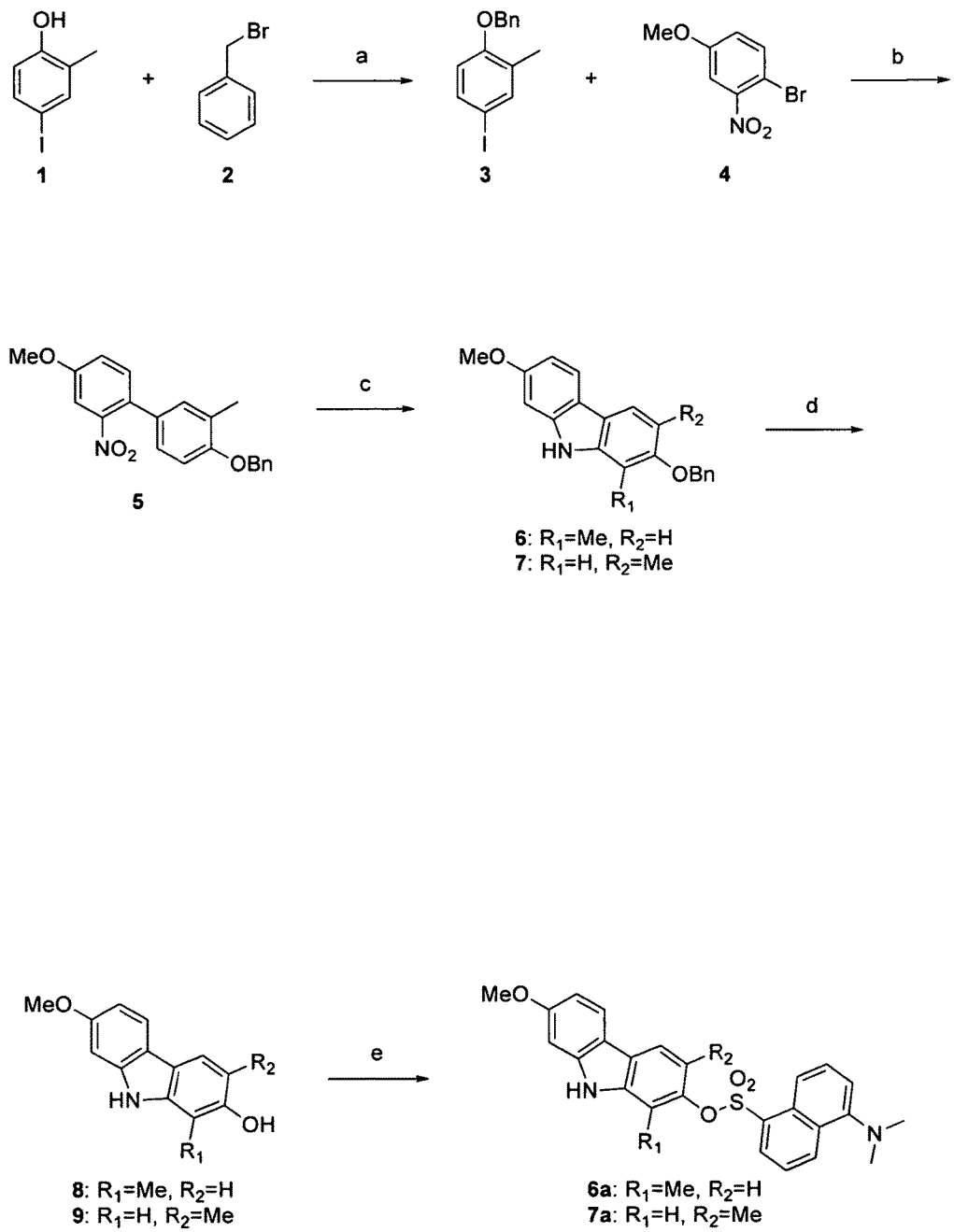
FIG. 5 shows the scheme for the synthesis of compounds 6a and 7a. Reagents: (a) $K_2CO_3$, MeCN; (b) palladium acetate, $K_2CO_3$, PEG; (c) $PPh_3$, 1,3-dichlorobenzene; (d) Pd/C (5% wt), ammonium formate, MeOH; (e) dansyl chloride, TEA, DCM.

1-(Benzyloxy)-4-iodo-2-methylbenzene (FIG. 5: compound 3). In 50 mL DMF were combined 4-iodo-2-methylphenol (5.00 g, 21.4 mmol) and anhydrous potassium carbonate (14.8 g, 106.8 mmol). After stirring 10 min, benzyl bromide (7.61 mL, 64.1 mmol) was added. The mixture was heated to 90° C. and stirred until complete by TLC (1-2 hr). Once cool, the reaction was filtered through a plug of Celite, washing with ethyl acetate. After removing the majority of the DMF under pressure, water was added (50 mL) and the aqueous layer extracted with 2×50 mL ethyl acetate. The organic layer was washed with 3×50 mL saturated aqueous lithium chloride then dried over magnesium sulfate. The solvent was removed and the resulting residue recrystallized in ethanol and hexanes to give the protected alcohol as shiny, off-white crystals (4.92 g, 71%). $^1$H NMR (400 MHz, CDCl$_3$): δ 7.45-7.33 (m, 7H), 6.64 (d, J=8.4 Hz, 1H), 5.06 (s, 2H), 2.23 (s, 3H); $^{13}$C NMR (100.6 MHz, CDCl$_3$): δ 156.72, 139.09, 136.87, 135.43, 129.90, 128.53, 127.86, 127.02, 113.60, 82.88, 69.87, 16.04; mp 58° C.

4'-(Benzyloxy)-4-methoxy-3'-methyl-2-nitrobiphenyl (FIG. 5: compound 5). Under vacuum, PEG 4600 (70.9 g, 15.4 mmol) was heated to 120° C. for 24 hours. Switching to a nitrogen atmosphere, compound 3 (5.00 g, 15.4 mmol), 4-bromo-3-nitroanisole (7.16 g, 30.8 mmol), anhydrous potassium carbonate (4.26 g, 30.8 mmol) and palladium acetate (0.17 g, 0.77 mmol) were added and the reaction allowed to stir at 120° C. for another 48 hours. Cooling the mixture resulted in a brown solid that was crushed using mortar and pestle and extracted with ether using a Soxhlet extraction apparatus. The solvent was removed and the resulting yellow residue purified via column chromatography to give the product as bright yellow crystals (2.16 g, 40%). $^1$H NMR (400 MHz, CDCl$_3$): δ 7.46 (d, J=7.2 Hz, 2H), 7.40 (t, J=7.2 Hz, 2H), 7.35-7.31 (m, 3H), 7.12 (dd, J$_S$=2.8 Hz, J$_L$=8.4 Hz, 1H), 7.10 (d, J=2.0 Hz, 1H), 7.06 (dd, J$_S$=2.0 Hz, J$_L$=8.4 Hz, 1H), 6.90 (d, J=8.0 Hz, 1H), 5.11 (s, 2H), 3.89 (s, 3H), 2.30 (s, 3H); $^{13}$C NMR (100.6 MHz, CDCl$_3$): δ 158.90, 156.98, 149.87, 137.44, 132.99, 130.57, 129.47, 128.76, 128.60, 128.05, 127.66, 127.36, 126.58, 118.79, 111.53, 109.03, 70.10, 56.11, 16.72; mp 119° C.

2-(Benzyloxy)-7-methoxy-1-methyl-9H-carbazole (FIG. 5: compound 6) and 2-(benzyloxy)-7-methoxy-3-methyl-9H-carbazole (FIG. 5: compound 7). Compound 5 (0.50 g, 1.4 mmol) was dissolved in 2 mL of 1,3-dicholorobenzene (1,3-DCB). The solution was purged with nitrogen and put under a nitrogen atmosphere. To this was added triphenylphosphine (0.94 g, 3.6 mmol) and the reaction refluxed for 48 hours. The 1,3-DCB was removed under vacuum and the residue re-dissolved in chloroform and impregnated on silica gel. Purification via column chromatography gave both cyclization products: (compound 6) as a yellowish solid (0.22 g). $^1$HNMR (400 MHz, CDCl$_3$): δ 7.84 (d, J=8.4 Hz, 1H), 7.76 (s, 1H), 7.73 (d, J=8.4 Hz, 1H), 7.50 (d, J=7.6 Hz, 2H), 7.41 (t, J=7.6 Hz, 2H), 7.34 (m, 1H), 6.93 (d, J=2.0 Hz, 1H), 6.91 (d, J=8.4 Hz, 1H), 6.83 (dd, J$_S$=2.0 Hz, J$_L$=8.4 Hz, 1H), 5.18 (s, 2H), 3.90 (s, 3H), 2.44 (s, 3H); $^{13}$C NMR (100.6 MHz, CDCl$_3$): δ 158.21, 154.40, 141.09, 140.27, 137.76, 128.46, 127.71, 127.29, 120.33, 117.90, 117.67, 116.88, 107.96, 107.69, 106.14, 95.00, 71.33, 55.60, 10.12; mp 167-168° C. (C$_{21}$H$_{19}$NO$_2$) C, H, N. C: calcd, 79.47; found, 77.98; and compound 7 as a light tan solid (0.20 g) for a total yield of 92%. $^1$H NMR (400 MHz, CDCl$_3$): δ 7.80 (d, J=8.4 Hz, 1H), 7.76 (s, 1H), 7.72 (s, 1H), 7.49 (d, J=7.2 Hz, 2H), 7.41 (t, J=7.2 Hz, 2H), 7.33 (m, 1H), 6.89 (s, 1H), 6.87 (d, J=2.4 Hz, 1H), 6.81 (dd, J$_S$=2.4 Hz, J$_L$=8.4 Hz, 1H), 5.16 (s, 2H), 3.88 (s, 3H), 2.42 (s, 3H); $^{13}$C NMR (100.6 MHz, DMSO-d$_6$): δ 157.25, 154.53, 140.69, 139.13, 137.56, 128.33, 127.51, 127.11, 120.38, 119.64, 117.34, 116.30, 115.66, 107.05, 94.47, 94.26, 69.20, 55.10, 16.59; mp 250-251° C. (C$_{21}$H$_{19}$NO$_2$) C, H, N. C: calcd, 79.47; found, 78.60.

7-Methoxy-1-methyl-9H-carbazol-2-ol (FIG. 5: compound 8). In 5 mL of methanol was dissolved compound 6 (0.051 g, 0.16 mmol). The solution was purged with nitrogen and put under a nitrogen atmosphere. Ammonium formate (0.10 g, 1.6 mmol) was added along with a scoop of palladium on activated carbon (5% by weight). After stirring the mixture for 3 hours, it was filtered through a plug of Celite, washing with methanol and ethyl acetate. The solvent was removed under vacuum and the resulting residue re-dissolved in 20 mL ethyl acetate and washed 3×20 mL water. The organic layer was dried over magnesium sulfate and the solvent removed. Column chromatography provided the product as yellowish tan solid (0.038 g, 100%). $^1$H NMR (400 MHz, DMSO-d$_6$): δ 10.73 (s, 1H), 9.08 (s, 1H), 7.75 (d, J=8.4 Hz, 1H), 7.55 (d, J=8.4 Hz, 1H), 6.89 (d, J=2.4 Hz, 1H), 6.69 (dd, J$_S$=2.4 Hz, J$_L$=8.4 Hz, 1H), 6.65 (d, J=8.4 Hz, 1H), 3.80 (s, 3H), 2.29 (s, 3H); $^{13}$C NMR (100.6 MHz, DMSO-d$_6$): δ 157.05, 152.55, 141.03, 119.47, 117.29, 116.47, 115.10, 113.60, 107.93, 106.61, 104.74, 94.58, 55.19, 10.22; mp 200-202° C. (decomp). (C$_{14}$H$_{13}$NO$_2$) C, H, N. C: calcd, 73.99; found, 73.43.

7-Methoxy-3-methyl-9H-carbazol-2-ol (FIG. 5: compound 9). The above procedure was followed using compound 7 (0.11 g, 0.35 mmol). Column chromatography provided the product as an off-white chalky solid (0.082 g, 100%). $^1$H NMR (400 MHz, DMSO-$d_6$): δ 10.66 (s, 1H), 9.18 (s, 1H), 7.73 (d, J=8.4 Hz, 1H), 7.60 (s, 1H), 6.84 (d, J=2.4 Hz, 1H), 6.82 (s, 1H), 6.66 (dd, $J_S$=2.4 Hz, $J_L$=8.4 Hz, 1H), 3.79 (s, 3H), 2.22 (s, 3H); $^{13}$C NMR (100.6 MHz, DMSO-$d_6$): δ 156.96, 153.45, 140.54, 139.45, 120.27, 119.23, 116.68, 115.79, 114.97, 106.58, 96.02, 94.42, 55.10, 16.40; mp 238-240° C. (decomp). ($C_{14}H_{13}NO_2$) C, H, N. C: calcd, 73.99; found, 73.45.

7-Methoxy-1-methyl-9H-carbazol-2-yl 5-(dimethylamino)naphthalene-1-sulfonate (FIG. 5: compound 6a). Compound 8 (0.15 g, 0.66 mmol) was dissolved in DCM then TEA (0.18 mL, 1.3 mmol) was added and the reaction stirred for an hour. Dansyl chloride (0.18 g, 0.66 mmol) was added and after 3 hours the solvent was removed and the residue impregnated onto silica gel. Column chromatography gave the dansylated product as a fluffy yellow solid (0.30 g, 99%). $^1$HNMR (400 MHz, CDCl$_3$): δ 8.62 (d, J=8.4 Hz, 1H), 8.55 (d, J=8.4 Hz, 1H), 8.09 (d, J=7.6 Hz, 1H), 7.95 (s, 1H), 7.75 (d, J=8.4 Hz, 1H), 7.65 (t, J=7.6 Hz, 1H), 7.45 (m, 2H), 7.24 (m, 1H), 6.89 (s, 1H), 6.79 (d, J=8.4 Hz, 1H), 6.33 (d, J=8.4 Hz, 1H), 3.85 (s, 3H), 2.91 (s, 6H), 2.40 (s, 3H); $^{13}$C NMR (100.6 MHz, CDCl$_3$): δ 159.02, 151.82, 145.35, 141.32, 139.32, 132.00, 131.77, 130.91, 130.14, 129.83, 128.93, 123.02, 121.58, 121.08, 119.74, 117.02, 116.81, 115.59, 113.87, 113.57, 108.68, 94.78, 55.60, 45.43, 11.30; mp 174° C. Anal. ($C_{26}H_{24}N_2O_4S$) C, H, N.

7-Methoxy-3-methyl-9H-carbazol-2-yl 5-(dimethylamino)naphthalene-1-sulfonate (FIG. 5: compound 7a). The above procedure was followed using compound 9 (0.020 g, 0.90 mmol). Column chromatography provided the dansylated product as a yellow solid (0.032 g, 79%). $^1$H NMR (400 MHz, DMSO-$d_6$): δ 10.96 (s, 1H), 8.66 (d, J=8.4 Hz, 1H), 8.38 (d, J=8.4 Hz, 1H), 8.13 (d, J=7.6 Hz, 1H), 7.89 (d, J=8.4 Hz, 1H), 7.85 (s, 1H), 7.78 (t, J=8.0 Hz, 1H), 7.66 (t, J=8.0 Hz, 1H), 7.37 (d, J=7.6 Hz, 1H), 6.86 (d, J=2.4 Hz, 1H), 6.74 (dd, $J_S$=2.4 Hz, $J_L$=8.4 Hz, 1H), 6.58 (s, 1H), 3.80 (s, 3H), 2.90 (s, 6H), 2.23 (s, 3H); $^{13}$C NMR (100.6 MHz, DMSO-$d_6$): δ 158.52, 151.58, 145.06, 141.71, 137.73, 131.83, 131.26, 130.60, 129.18, 129.06, 128.99, 123.46, 121.46, 120.90, 120.81, 120.72, 118.44, 115.54, 115.07, 107.98, 103.34, 94.29, 55.07, 44.97, 16.39; mp 242° C.

Methyl-protected, methyl-down mahanine (FIG. 5: compound 10). In 1 mL of pyridine, compound 8 (0.061 g, 0.26 mmol) was combined with citral (0.09 mL, 0.53 mmol). The reaction was brought to reflux overnight then the solvent removed under vacuum. The resulting residue was re-dissolved in DCM and washed with 3×10 mL water. The organic layer was dried over magnesium sulfate and purified via column chromatography to yield the product as a yellow solid (0.0040 g, 4%). $^1$H NMR (400 MHz, CDCl$_3$): δ 7.77 (d, J=8.4 Hz, 1H), 7.74 (s, 1H), 7.40 (s, 1H), 6.90 (d, J=2.4 Hz, 1H), 6.80 (dd, $J_S$=2.4 Hz, $J_L$=8.4 Hz, 1H), 6.51 (d, J=10.0 Hz, 1H), 5.54 (d, J=10.0 Hz, 1H), 5.11 (m, 1H), 3.88 (s, 3H), 2.35 (s, 3H), 2.16 (m, 2H), 1.73 (m, 2H), 1.65 (s, 3H), 1.57 (s, 3H), 1.43 (s, 3H); $^{13}$C NMR (100.6 MHz, CDCl$_3$): δ 131.51, 129.02, 127.44, 124.32, 124.09, 120.06, 118.24, 116.31, 115.10, 114.44, 107.73, 104.77, 95.11, 78.31, 55.64, 41.04, 27.31, 26.13, 25.66, 22.76, 21.70, 17.57, 9.51; mp ° C.

Material and Methods 2: Biology

Cell Line and Cell Growth Assay. Human prostate cancer cell line PC-3 was procured from the American Type Cell Culture Collection (Manassas, Va.). Cells were grown in IMEM without phenol red (Invitrogen, Carlsbad, Calif.) with 10% fetal bovine serum, 2 mM glutamine, 100 U/mL penicillin G sodium, and 100 µg/mL streptomycin sulfate (Sigma, St. Louis, Mo.) in the presence of 5% $CO_2$ at 37° C.

For the cell growth experiment, PC-3 cells were seeded in 6-well plates in triplicate with an initial density of 2×10$^3$ cells per well. Twenty-four hours after seeding, the attached cells were treated with vehicle (DMSO) or 1, 5, 15, 30 and 60 µM compound. After another twenty-four hours, the cells were washed with 1×PBS, trypsinized and re-suspended in complete growth medium. Trypan blue (0.4%) was added to the cell suspension and both live and dead cells were counted using a hemocytometer.

BrdU Labeling. For the BrdU experiment, PC-3 cells were seeded in 96-well plates at a density of 2×10$^3$ cells/well, treated with 5 µM of compound for 24 hr and assayed BrdU using the Cell Proliferation ELISA BrdU (chemiluminescence) (Roche Diagnostics, IN) kit according to the manufacturer's protocol. Briefly, 10 µL of 100 µM BrdU labeling solution was added to the cultured cells and were incubated for 1 hr at 37° C., the labeling solution was removed and the FixDenat solution provided with the kit was added for 30 min and incubated at room temperature. Cells were then incubated with anti-BrdU conjugated to peroxidase (1:1500) for 60 min. Finally, the plates were washed and 100 µL of substrate solution was added to each well, and the light emission was measured using a microplate luminometer (Harta Instruments, Inc., Gaithersburg, Md.).

Reverse Transcriptase-polymerase Chain Reaction (RT-PCR). From PC-3 cells incubated 24 hours with either 15 µM of compound 6, 7, 7a, 8, 9, 10 or 5 µM of KED-4-69 (compound 6a), RNA was extracted with TRIzol solution (Invitrogen, Carlsbad, Calif.) and genes of interest were amplified using 500 ng of total RNA reverse-transcribed to cDNA using a Superscript II kit (Invitrogen) with random hexamers. Human-specific primers were designed using the Primer Quest program and purchased from Integrated DNA Technologies, Inc. (Coralville, Iowa). Their sequences and product band sizes are: cyclin D1 forward primer 5'-CACACGGACTACAGGGGAGT-3' (SEQ ID NO:1), cyclin D1 reverse primer 5'-AGGAAGCGGTCCAGGTAGTT-3' (SEQ ID NO:2) (475 bp) and GAPDH forward primer: 5'-CCA CCCATGGCAAATTCCATGGCA-3' (SEQ ID NO:3), GAPDH reverse primer: 5'-TCTAGACGGCAG GTCAGGTCCACC-3' (SEQ ID NO:4) (598 bp). PCRs were initiated at 94° C. for 2 min, followed by 28 cycles of 94° C. for 1 min, 1 min annealing temperature, 72° C. for 1 min, and final extension at 72° C. for 5 min. The annealing temperature for cyclin D1 and GAPDH was 60° C. Primers and PCR conditions for RASSF1A are used as described by Rong et al. (*Oncogene.* 2004, 23, 8216-8230). After amplification, PCR products were separated on 1.5% agarose gels and visualized by ethidium bromide fluorescence using the Fuji LAS-1000 Imager. Images were captured and imported to Adobe Photoshop. Band intensities were quantified by using ImageJ software (NIH, Bethesda, Md.).

DNA methyltransferase activity assay. PC-3 cells were plated in complete growth media, treated with either mahanine or compound 6a at 2 µM or compound 6, 7, 7a, 8, 9, 10 at 15 µM for 3 days and then harvested. Nuclear extracts were prepared according to manufacturer's protocol (Nuclear extraction kit, Epigentek). DNMT activity was measured using an EpiQuik DNA methyltransferase activity assay kit (Epigentek). Results were expressed as percent DNMT activity compared to the DMSO control as 100%.

Multiphoton laser imaging. After incubating slides with a fibronectin/cortactin solution for 30 minutes, PC-3 cells were plated onto the slides and incubated overnight. The cells were then treated with a 5 µM solution of compound 6a or DMSO control and incubated for 1-6 hour before washing with PBS. The slides were fixed with a 4% formaldehyde solution, washed with PBS then treated with propidium iodide (nuclear localization) and DNMT3a or DNMT3b. The compound was excited at 725 nm with a multiphoton laser and imaged with a 500-550 nm filter.

Animals. Balb/c mice and athymic Balb/c nude mice were purchased from the National Cancer Institute (NCI). Animals were housed 4-6 per cage with microisolater tops and provided food (Furina mice chow) and water ad libitum. The light cycle was regulated automatically (12 hours light/dark cycle) and temperature was maintained at 23±1° C. All animals were allowed to acclimate to this environment for one week prior to experimental manipulations. The Georgetown University Animal Care and Use Committee approved all animal studies in accordance with the guidelines adopted by the National Institute of Health.

Cell Culture for Xenograft. PC-3 cell line (ATCC, Manassas, Va.) was cultured in RPMI-1640 with L-glutamine (Mediatech Inc., Herdon, Va.) containing 5% fetal bovine serum (FBS), 2.5 mM L-glutamine at 37° C. with 5% $CO_2$.

Xenograft Study. Male athymic Balb/c nude mice (18-22 g) were injected with 3×106 (0.3 mL) of the human prostate cancer cells (PC-3). The human prostate cancer cells were injected in the subcutaneous tissue of the right axillary region of the mice. One week after the injection, the mice were randomly sorted into two groups with four mice per group. A stock solution of compound 6a was obtained by dissolving 1 mg of compound in 1 µl DMSO. The stock was added to polyethylene glycol 400 (PEG) (Hampton) and PBS in a 1:1 ratio. The test concentrations were obtained by diluting with PEG/PBS. The tumor-bearing mice received an intraperitoneal injection (IP) with either 10 mg/kg of 6a or vehicle control once every other day for 4 weeks. At the same time, the tumor size of each mouse was measured by caliper and calculated by the formula: Length×width× height/2.

Statistical Analyses. All data were derived from at least three independent experiments and statistical analyses were conduced using Prism 3 GraphPad software (La Jolla, Calif.). Values were presented as means±SEM. Significance level was calculated using the one-way analysis of variance (ANOVA) followed be the Dunnett's post test with an assigned confidence interval of 95%. p-value <0.05 was considered significant.

Example 1

Synthesis of RASSF1A Inhibitors

Figure 6:
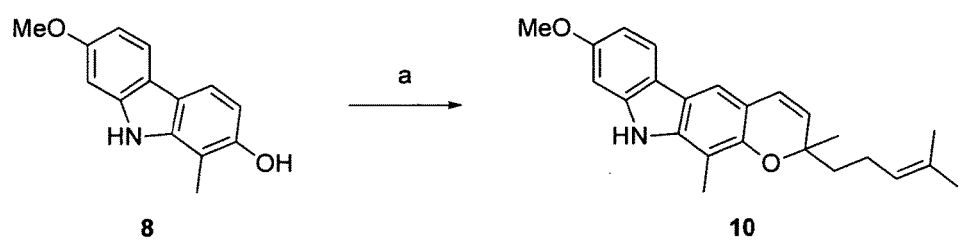
FIG. 6 shows the scheme for the synthesis of compound 10. Reagents: (a) citral, pyridine.

In the pursuit of new RASSF1A inhibitors, modifications off of a carbazole backbone were selected as the primary focus due to the synthetic challenge and uncommon carbazole structure. Synthetically, we envisioned the formation of the carbazole moiety through the cyclization of a bi-aryl system. After the failure of many typical coupling reactions (Negishi, Suzuki, Kumada) attempted in the cross-coupling of respectively functionalized variants of compounds 3 and 4 (FIG. 5), a substrate-specific reaction from Wang, L., et al., was found to be applicable to our system of aryl halides (compound 5; Wang, L. et al. *J. Org. Chem.* 2006, 71, 1284-1287). The resulting bi-aryl 5 was then cyclized with a procedure from Freeman, A. W., et al., to give the two possible regioisomers, compounds 6 and 7 (Freeman et al. *J. Org. Chem.* 2005, 70, 5014-5019). We found that by varying the solvent and the equivalents of triphenylphospine ($PPh_3$), different ratios of compounds 6 to 7 were achieved. Use of 1,3-dichlorobenzene (DCB) and 2.5 eq of $PPh_3$ gave the more sterically-hindered compound 6 in excess (60:40), whereas 1,2-DCB with 3-5 eq $PPh_3$ provided the less sterically-hindered compound 7 in a slight excess (45:55). A palladium-on-carbon-mediated deprotection of the benzyl groups of compounds 6 and 7 provided the alcohol compounds 8 and 9, which were dansyl-protected to give the fluorescent analogs compounds 6a and 7a. Cyclization of compound 8 with citral gave the racemic mahanine analog compound 10 (FIG. 6). In compound 10, the free alcohol present in mahanine is methyl-protected, and the relative positions of the methyl group and cyclic ether moiety are swapped from that of mahanine.

Example 2

Mahanine Precursors and Analog Inhibit Growth in Human Prostate Cells

Compounds 6-10 were screened for growth inhibition in PC-3 human prostate cancer cells using previously reported methods (Table 1; Sinha et al. *The Prostate*. 2006, 66, 1257-1265). Compound 6 and its derivatives compounds 6a and 8 show markedly improved inhibition over that of compounds 7 and 7a, despite varying by only the position of a methyl group (1-position versus 3-position). This was unexpected, since the methyl moiety of mahanine is in the 3-position. Compound 9, with its $GI_{50}$ value near that of the compound 6 series (compounds 6, 6a, 8) and a deprotected hydroxyl group in the 2-position, implies that whatever hindrance is imposed by a methyl in the 3-position can be partially overcome if steric bulk at the 2-position is reduced. Indeed, looking at the structure of mahanine, the restraint of the ether cycle may provide enough reduction of apparent bulk at the 2-position to moderate its methyl in the 3-position. Additionally, the ether ring system puts the equivalent of a methyl group in the 1-position, which could also be aiding in the low µM activity of mahanine, if the relatively lower values for the compound 6 series are any indication. Moreover, analyzing the structure of compound 10 based on the same criteria, the double-bonded carbon of the ether cycle in the 3-position along with bulk off the 2-position might explain its lesser growth inhibition when compared to mahanine, while the methyl in the 1-position still gives it better activity than compounds 7 and 7a.

Overall, of the compounds evaluated only compound 6a provided greater inhibitory effects than those of mahanine. Also, though mahanine was observed to be cytotoxic at higher doses (above 5 µM), compound 6a proved to be purely cytostatic, maintaining the initial cell count of time zero after 24 hours at concentrations up to 30 µM (data not shown). Thus, compound 6a lacks a higher dose toxicity in cells.

TABLE 1

$GI_{50}$ values for mahanine and synthesized compounds in treated human prostate cancer cells.[a]

| Compound | $GI_{50}$ (µM) |
| --- | --- |
| Mahanine | 2.5 ± 0.18 |
| 6 | 17.6 ± 2.7 |
| 6a | 1.5 ± 0.11 |
| 7 | 48.9 ± 1.1 |
| 7a | 22.9 ± 4.5 |
| 8 | 18.7 ± 1.8 |

TABLE 1-continued

GI$_{50}$ values for mahanine and synthesized compounds in treated human prostate cancer cells.[a]

| Compound | GI$_{50}$ (µM) |
|---|---|
| 9 | 15.3 ± 2.8 |
| 10 | 11.3 ± 1.8 |

[a]Concentrations required for 50% growth inhibition in PC3 cells. Cells were plated in triplicate wells and exposed to various concentrations (0, 1, 5, 15, 30, 60 µM) of each compound. After 24 hours of treatment, viable cells (as assessed by trypan blue dye exclusion assay) were counted using a hemocytometer. Values are the mean ± SEM of three independent observations.

Example 3

Active Compounds Show Decrease in DNA Synthetic Ability

To assess the levels of DNA synthesis within cells treated with mahanine compared to those treated with compounds 6-10, cultured cells were treated according to standard procedure with 5-bromo-2-deoxy-uridine (BrdU) after 24 hours of treatment (FIG. 2). Only three synthetic compounds paralleled mahanine in causing a decrease in DNA synthetic ability: compounds 6, 6a and 9. Since DNA synthetic ability is associated with cell proliferation, it was not surprising that cells treated with compound 6 and 6a exhibit less proliferation than those treated at 5 µM with compound 7 or 7a, given the higher inhibitory concentration values of the latter two compounds. However, it is noteworthy that the growth inhibition for compounds 8 and 10, which have inhibitory concentrations around or below that of compound 9, appear to be separate from any effect on proliferation, since no change in the DNA synthetic ability of cells treated with the compounds indicates the cells are still reproducing.

Example 4

Up-Regulation of RASSF1A and Down-Regulation of Cyclin D1

Figure 3:
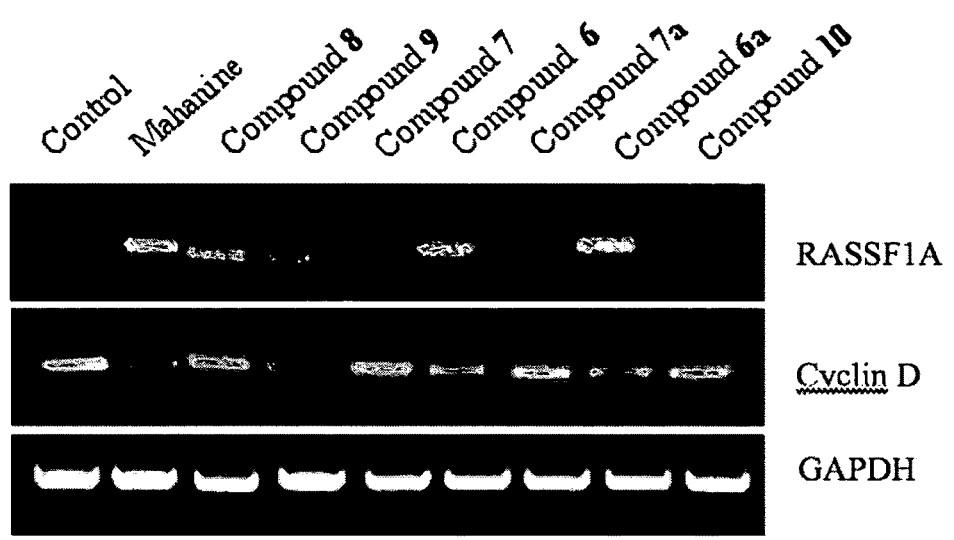
FIG. 3 shows that mahanine analogs induce RASSF1A expression and downregulate cyclin D1. Representative photograph of an experiment repeated thrice. PC-3 cells were treated 24 hours with either 15 μM for compounds 6, 7, 7a, 8, 9, 10 or 5 μM for compound KED-4-69 (compound 6a) before RNA extraction and RT-PCR amplification.

It has been reported that mRNA levels of RASSF1A correlate to its protein expression levels (Rong et al. Oncogene, 2004, 23: 8216-8230). To investigate the effects of the synthetic compounds on RASSF1A and cyclin D1 expression, levels of the respective mRNAs in treated cells compared to control were analyzed (FIG. 3). Compounds 6 and 6a displayed profiles identical to that of mahanine: a significant increase in RASSF1A with a corresponding decrease in cyclin D1. This same increase/decrease was also observed for compounds 8 and 9, but to a lesser extent. Because overexpression of cyclin D1 is associated with tumorigenicity and proliferation in a variety of tumors, including prostate cancers, this downregulation provides a cancer treatment method (Chen, Y. et al. Oncogene. 1998, 16, 1913-1920; Musgrove, E. A. et al. Proc. Natl. Acad. Sci. USA. 1994, 91, 8022-8026). Compounds 7, 7a and 10 show no change in expression levels from control.

Example 5

Synthetic Compounds Inhibit DNA Methyltransferase Activity

Figure 7:
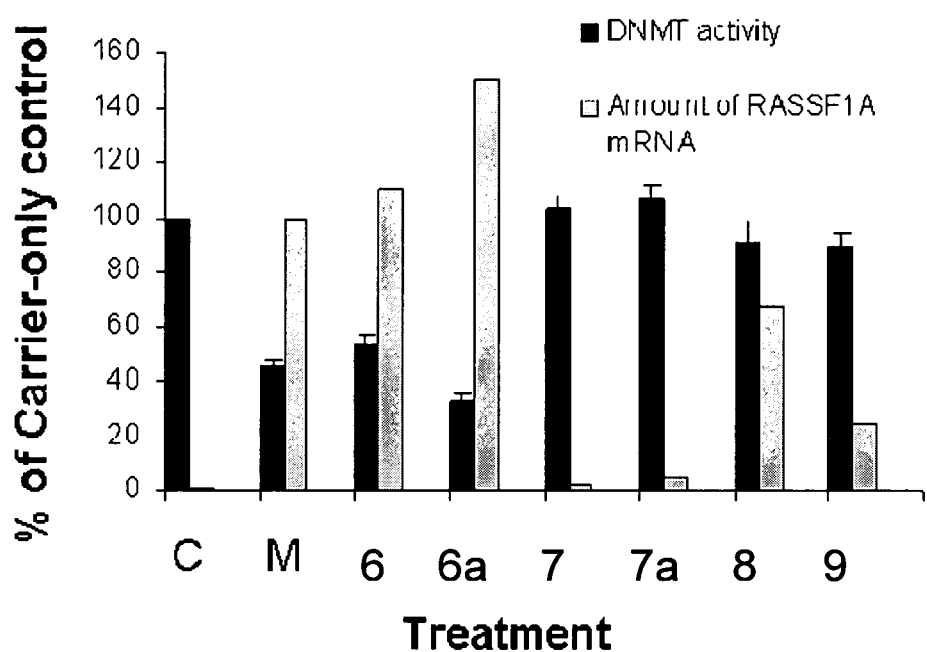
FIG. 7 shows that mahanine analogs that up-regulate RASSF1A also inhibit DNA methyltransferase activity. Black bars: PC-3 cells were treated 72 hours with either mahanine or compound 6a at 5 μM or compound 6, 7, 7a, 8, or 9 at 15 μM and then assayed for DNMT activity using the DNMT activity kit from Epigentek. Data are mean of three independent experiments ±SEM. Grey bars: Densitometry from RT-PCR blot where the amount of RASSF1A mRNA re-expressed by mahanine treatment is normalized to 100%.

The levels of DNMT activity in treated versus untreated prostate cancer cells were measured using a DNMT assay kit from Epigentek. Significant inhibition of DNMT activity was observed with mahanine and compounds 6 and 6a, with compound 6a causing the most potent inhibition (FIG. 7, black bars). A slight decrease in DNMT activity was also associated with compounds 8 and 9. These reduced DNMT activities correlate with the pattern of RASSF1A induction described above (FIG. 7, grey bars). The data imply that inhibition of DNMT prevents hypermethylation of the RASSF1A promoter region and consequently restores RASSF1A.

Example 6

Figure 4:
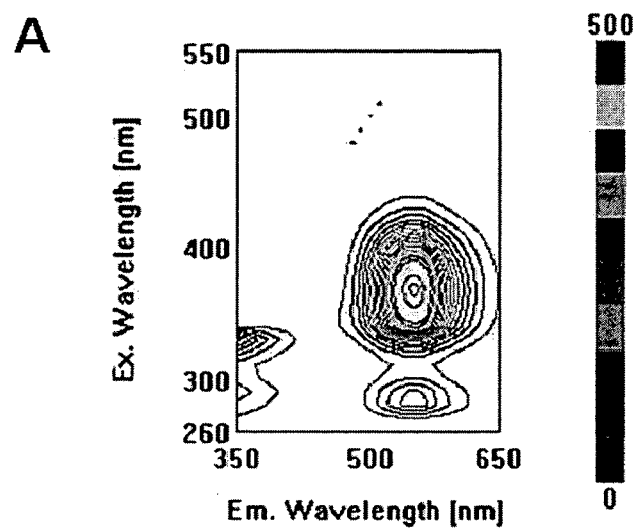
FIGS. 4A-D show that fluorescent compound 6a is seen exclusively in the cytoplasm of PC-3 cells and appears to sequester DNMT3b in the cytoplasm. (A) Fluorescent spectrum of compound 6a; (B) PC-3 cells were treated with a 5 μM solution of compound 6a for 1 hr before being fixed and stained with propidium iodide and DNMT3b antibody; (C) Cells were treated with a 5 μM solution of compound 6a for 6 hr before fixation; (D) Cells were treated with a 5 μM solution of DMSO for 6 hr before fixation. The frames in each set of images are from left to right, top to bottom: propidium iodide; clear field; DNA methyltransferase 3b (DNMT3b); compound 6a or vehicle; and merged. Compound 6a was excited at 725 nm with a multiphoton laser and imaged with a 500-550 nm filter. Arrows indicate representative cells in which DNMT3b is solely in the cytoplasm.
Figure 4:
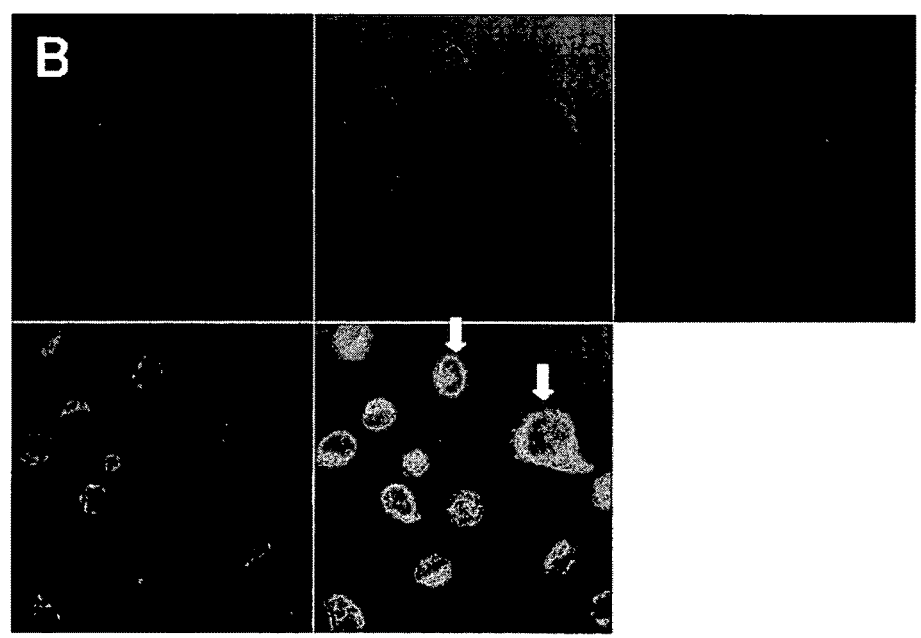
Figure 4:
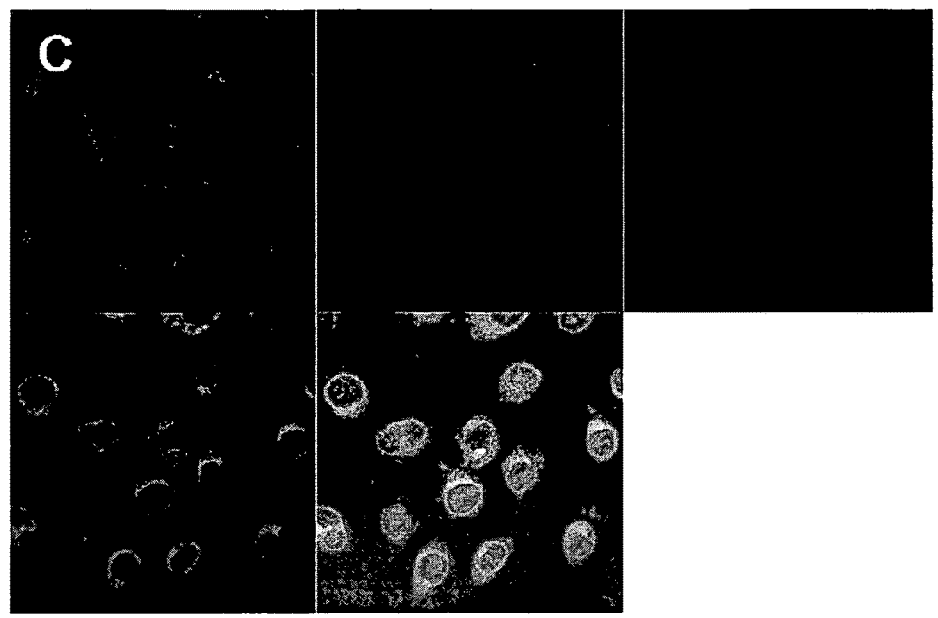
Figure 4:
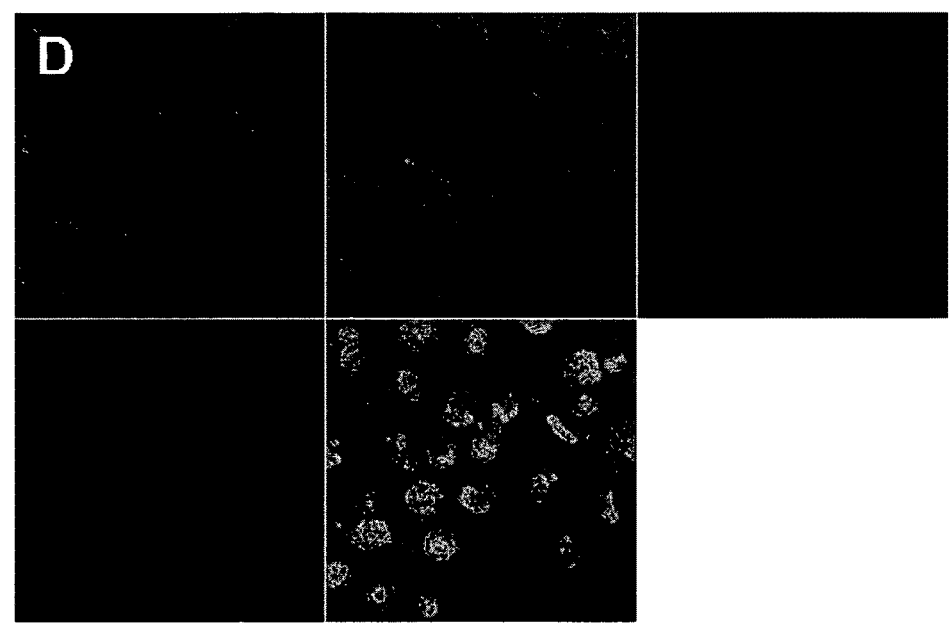

Fluorescent Analog Confirms Intracellular Delivery and Reveals Cellular Localization The dansyl moiety present in compound 6a allows it to visibly fluoresce at 552 nm when excited at 370 nm (FIG. 4A). After treating PC-3 cells with compound 6a, a multiphoton laser was used to excite the compound, and its emission from within the cells was observed by confocal microscopy (FIG. 4B-D). With propidium iodide staining the nuclei of the cells, it is apparent that compound 6a is present within the cytoplasm of the cells but not in the nuclei (FIG. 4B,C). To further confirm the hypothesis that compound 6a interaction with DNMT is a crucial factor in the ultimate up-regulation of RASSF1A, the cell samples were stained with antibodies for the DNMT isoforms known to shuttle between the nucleus and the cytoplasm, DNMT3a and DNMT3b (Kim et al., EMBO J, 2002, 21: 4183-4195; Majumber et al., JBC, 2002, 277: 16048-16058). Interestingly, while DNMT3b is present in both the cytoplasm and nuclei of the control cells (FIG. 4D), after one hour there was a population of treated cells that have DNMT3b only in the cytoplasm (FIG. 4B, arrows). By six hours this effect is very pronounced, with the majority of treated cells having DNMT3b only in the cytoplasm (FIG. 4C). No corresponding effect was seen with DNMT3a (data not shown), making it unlikely that it is a global inhibition of nuclear access. Thus, cytoplasmic sequestering of DNMT3b is implied as a mode of action for compound 6a.

Example 7

Figure 8:
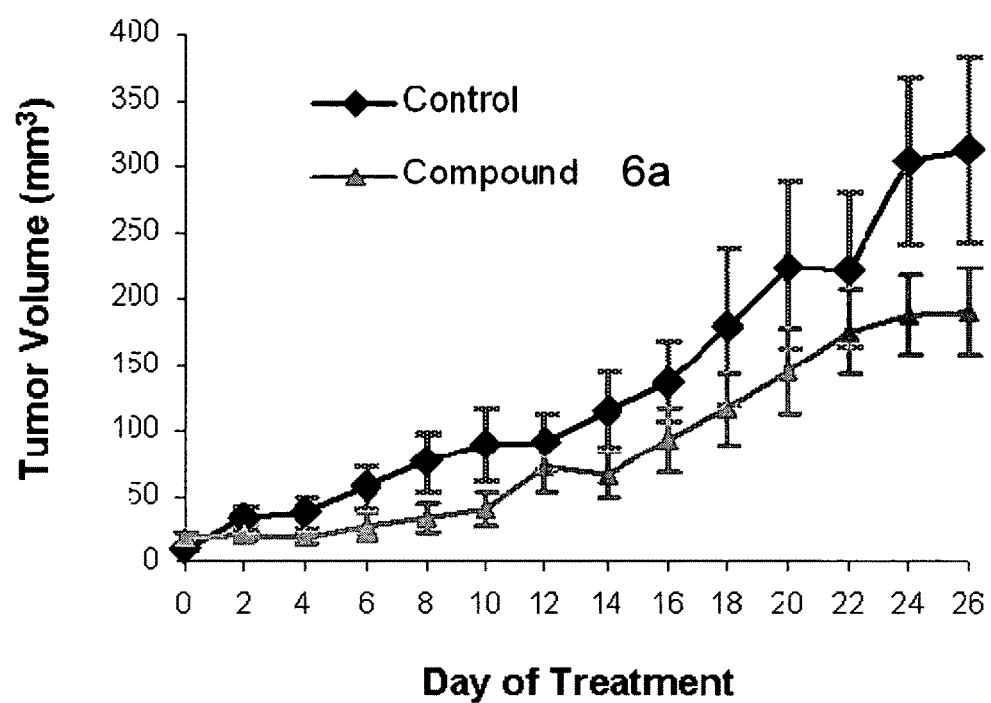
FIG. 8 shows that treatment with compound 6a reduces the volume of human prostate xenograft tumors. Male athymic Balb/c nude mice were injected with PC-3 cells and the resulting tumors allowed to grow for a week before dosing IP once a day every other day with 10 mg/kg compound 6a or DMSO control in 1:1 PEG/PBS. Data are presented as the mean±SEM (n=4).

In Vivo Studies Indicate a Large Therapeutic Index and Significant Volume Reduction of Human Prostate Xenograft Tumors in Mice Treated with Compound 6a Using the Acute oral toxicity up-and-down procedure, no toxicity was observed for compound 6a in wild-type Balb/c mice dosed up to 550 mg/kg (Acute Oral Toxicity (AOT) Up-And-Down-Procedure; http://www.epa.gov/oppfead1/harmonization). This provided an ample therapeutic index of >55 at a starting efficacy dose of 10 mg/kg. Athymic Balb/c nude mice with human prostate tumor xenografts were dosed via intraperitoneal injection with 10 mg/kg of compound 6a once a day every other day for 25 days. Control mice were dosed with vehicle alone. Compound 6a reduced tumor volume by roughly 40% compared to control over 25 days (FIG. 8). These results demonstrate the use of compound 6a for reducing human prostate tumor volume.

REFERENCES

1. Dammann R, Li C, Yoon J H, Chin P L, Bates S, Pfeifer G P. Epigenetic inactivation of a RAS association domain 1. family protein from the lung tumour suppressor locus 3p21.3. Nat Genet 2000; 25:315-9.
2. Burbee D G, Forgacs E, Zochbauer-Muller S, Shivakumar L, Fong K, Gao B, Randle D, Kondo M, Virmani A, Bader S, Sekido Y, Latif F, Milchgrub S, Toyooka S, Gazdar A F, Lerman M I, Zabarovsky E, White M, Minna J D. Epigenetic inactivation of RASSF1A in lung and breast cancers and malignant phenotype suppression. J Natl Cancer Inst 2001; 93:691-9.
3. Vos M D, Ellis C A, Bell A, Birrer M J, Clark G J. Ras uses the novel tumor suppressor RASSF1 as an effector to mediate apoptosis. J Biol Chem 2000; 275:35669-72.
4. Pfeifer G P, Yoon J H, Liu L, Tommasi S, Wilczynski S P, Dammann R. Methylation of the RASSF1A gene in human cancers. Biol Chem 2002; 383:907-14. Review.
5. Dammann R, Schagdarsurengin U, Strunnikova M, Rastetter M, Seidel C, Liu L, Tommasi S, Pfeifer G P. Epigenetic inactivation of the Ras-association domain family 1 (RASSF1A) gene and its function in human carcinogenesis. Histol Histopathol 2003; 18:665-77.
6. Dammann R, Takahashi T, Pfeifer G P. The CpG island of the novel tumor suppressor gene RASSF1A is intensely methylated in primary small cell lung carcinomas. Oncogene 2001; 20:3 563-7.
7. Dammann R, Yang G, Pfeifer G P. Hypermethylation of the cpG island of Ras association domain family 1A (RASSF1A), a putative tumor suppressor gene from the 3p21.3 locus, occurs in a large percentage of human breast cancers. Cancer Res 2001; 61:3105-9.
8. Yan P S, Shi H, Rahmatpanah F, Hsiau T H, Hsiau A H, Leu Y W, Liu J C, Huang T H.
   Differential distribution of DNA methylation within the RASSF1A CpG island in breast cancer. Cancer Res 2003; 63:6178-86.
9. Schagdarsurengin U, Wilkens L, Steinemann D, Flemming P, Kreipe H H, Pfeifer G P, Schlegelberger B, Dammann R. Frequent epigenetic inactivation of the RASSF1A gene in hepatocellular carcinoma. Oncogene 2003; 22:1866-71.
10. Zhang Y J, Ahsan H, Chen Y, Lunn R M, Wang L Y, Chen S Y, Lee P H, Chen C J, Santella R M. High frequency of promoter hypermethylation of RASSF1A and p16 and its relationship to aflatoxin B1-DNA adduct levels in human hepatocellular carcinoma. Mol Carcinog 2002; 35:85-92.
11. Zhong S, Yeo W, Tang M W, Wong N, Lai P B, Johnson P J. Intensive hypermethylation of the CpG island of Ras association domain family 1A in hepatitis B virus-associated hepatocellular carcinomas. Clin Cancer Res 2003; 9:3376-82.
12. Liu L, Broaddus R R, Yao J C, Xie S, White J A, Wu T T, Hamilton S R, Rashid A. Epigenetic alterations in neuroendocrine tumors: methylation of RAS-association domain family 1, isoform A and p16 genes are associated with metastasis. Mod Pathol 2005; 18:1632-40.
13. Lo K W, Kwong J, Hui A B, Chan S Y, To K F, Chan A S, Chow L S, Teo P M, Johnson P J, Huang D P. High frequency of promoter hypermethylation of RASSF1A in nasopharyngeal carcinoma. Cancer Res 2001; 61:3877-81.
14. Dreijerink K, Braga E, Kuzmin I, Geil L, Duh F M, Angeloni D, Zbar B, Lerman M I, Stanbridge E J, Minna J D, Protopopov A, Li J, Kashuba V, Klein G, Zabarovsky E R. The candidate tumor suppressor gene, RASSF1A, from human chromosome 3p21.3 is involved in kidney tumorigenesis. Proc Natl Acad Sci USA 2001; 98:7504-9.
15. Lee M G, Kim H Y, Byun D S, Lee S J, Lee C H, Kim J I, Chang S G, Chi S G. Frequent epigenetic inactivation of RASSF1A in human bladder carcinoma. Cancer Res 2001; 61:6688-92.
16. Kuzmin I, Gillespie J W, Protopopov A, Geil L, Dreijerink K, Yang Y, Vocke C D, Duh F M, Zabarovsky E, Minna J D, Rhim J S, Emmert-Buck M R, Linehan W M, Lerman M I. The RASSF1A tumor suppressor gene is inactivated in prostate tumors and suppresses growth of prostate carcinoma cells. Cancer Res 2002; 62:3498-502.
17. Liu L, Yoon J H, Dammann R, Pfeifer G P. Frequent hypermethylation of the RASSF1A gene in prostate cancer. Oncogene 2002; 21:6835-40.
18. Maruyama R, Toyooka S, Toyooka K O, Virmani A K, Zochbauer-Muller S, Farinas A J, Minna J D, McConnell J, Frenkel E P, Gazdar A F. Aberrant promoter methylation profile of prostate cancers and its relationship to clinicopathological features. Clin Cancer Res 2002; 8:514-9.
19. Chow L S, Lo K W, Kwong J, To K F, Tsang K S, Lam C W, Dammann R, Huang D P. RASSF1A is a target tumor suppressor from 3p21.3 in nasopharyngeal carcinoma. Int J Cancer 2004; 109:839-47.
20. Li J, Wang F, Protopopov A, Malyukova A, Kashuba V, Minna J D, Lerman M I, Klein G, Zabarovsky E. Inactivation of RASSF1C during in vivo tumor growth identifies it as a tumorsuppressor gene. Oncogene 2004; 23:5941-9.
21. Hesson L, Bieche I, Krex D, Criniere E, Hoang-Xuan K, Maher E R, Latif F. Frequent epigenetic inactivation of RASSF1A and BLU genes located within the critical 3p21.3 region in gliomas. Oncogene 2004; 23:2408-19.
22. Khokhlatchev A, Rabizadeh S, Xavier R, Nedwidek M, Chen T, Zhang X F, Seed B, Avruch J. Identification of a novel Ras-regulated proapoptotic pathway. Curr Biol 2002; 12:253-65.
23. Liu L, Tommasi S, Lee D H, Dammann R, Pfeifer G P. Control of microtubule stability by the RASSF1A tumor suppressor. Oncogene 2003; 22:8125-36.
24. Song M S, Song S J, Ayad N G, Chang J S, Lee J H, Hong H K, Lee H, Choi N, Kim J, Kim H, Kim J W, Choi E J, Kirschner M W, Lim D S. The tumour suppressor RASSF1A regulates mitosis by inhibiting the APC-Cdc20 complex. Nat Cell Biol 2004; 6:129-37.
25. Jackson P K. Linking tumor suppression, DNA damage and the anaphase-promoting complex. Trends Cell Biol 2004;14:331-4. Review.
26. Rong R, Jin W, Zhang J, Sheikh M S, Huang Y. Tumor suppressor RASSF1A is a microtubule-binding protein that stabilizes microtubules and induces G2/M arrest. Oncogene 2004; 23:8216-30.
27. Tommasi S, Dammann R, Zhang Z, Wang Y, Liu L, Tsark W M, Wilczynski S P, Li J, You M, Pfeifer G P. Tumor susceptibility of Rassf1a knockout mice. Cancer Res 2005; 65:92-8.
28. Shivakumar L, Minna J, Sakamaki T, Pestell R, White M A. The RASSF1A tumor suppressor blocks cell cycle progression and inhibits cyclin D1 accumulation. Mol Cell Biol 2002; 22:4309-18.
29. Ahmed-Choudhury J, Agathanggelou A, Fenton S L, Ricketts C, Clark G J, Maher E R, Latif F. Transcriptional regulation of cyclin A2 by RASSF1A through the enhanced binding of p120E4F to the cyclin A2 promoter. Cancer Res 2005; 65:2690-7.
30. Whang Y M, Kim Y H, Kim J S, Yoo Y D. RASSF1A suppresses the c-Jun-NH2-kinase pathway and inhibits cell cycle progression. Cancer Res 2005; 65:3682-90.

31. Donn A S, Muir C S. Prostatic cancer: some epidemiological features. Bull Cancer 1985; 72:381-290.
32. Wingo P A, Landis S, Ries L A. An adjustment to the 1997 estimate for new prostate cancer cases. CA Cancer J Clin 1997; 47:239-242.
33. Sinha S, Pal B C, Jagadeesh S, Banerjee P P, Bandyopadhaya, and Bhattacharya S. Mahanine inhibits growth and induces apoptosis in prostate cancer cells through the deactivation of Akt and activation of caspases. Prostate 2006; 661257-65.
34. Lee M G, Kim H Y, Byun D S, Lee S J, Lee C H, Kim J I, Chang S G, Chi S G. Frequent epigenetic inactivation of RASSF1 A in human bladder carcinoma. Cancer Res 2001; 61:6688-92.
35. Albanese C, Johnson J, Watanabe G, Eklund N, Vu D, Arnold A, Pestell R G. Transforming p21ras mutants and c-Ets-2 activate the cyclin D1 promoter through distinguishable regions. J Biol Chem 1995; 270:23589-97.
36. Song M S, Song S J, Ayad N G, Chang J S, Lee J H, Hong H K, Lee H, Choi N, Kim J, Kim H, Kim J W, Choi E J, Kirschner M W, Lim D S. The tumour suppressor RASSF1A regulates mitosis by inhibiting the APC-Cdc20 complex Nat Cell Biol. 2004; 6:129-37.
37. M. Fu, C. Wang, Z. Li, T. Sakamaki, R. G. Pestell, Minireview: Cyclin D1: normal and abnormal functions. Endocrinology 2004; 145: 5439-47.
38. M. Shtutman, J. Zhurinsky, I. Simcha, C. Albanese, M. D'Amico, R. Pestell, A. Ben-Ze'ev, The cyclin D1 gene is a target of the beta-catenin/LEF-1 pathway. Proc Natl Acad Sci USA 1999; 96:5522-27.
39. J. A. Diehl, M. Cheng, M. F. Roussel, C. J. Sherr, Glycogen synthase kinase-3beta regulates cyclin D1 proteolysis and subcellular localization. Genes Dev 1998; 12: 3499-3511.
40. H. Koike, K. Suzuki, T. Satoh, N. Ohtake, T. Takei, S. Nakata, H. Yamanaka, Cyclin D1 gene polymorphism and familial prostate cancer: the AA genotype of A870G polymorphism is associated with prostate cancer risk in men aged 70 years or older and metastatic stage. Anticancer Res 2003; 23: 4947-51.
41. M. Drobnjak, I. Osman, H. I. Scher, M. Fazzari, C. Cordon-Cardo, Overexpression of cyclin D1 is associated with metastatic prostate cancer to bone. Clin Cancer Res 2000; 6:1891-95.
42. Y. Chen, L. A. Martinez, M. LaCava, L. Coghlan, C. J. Conti, Increased cell growth and tumorigenicity in human prostate LNCaP cells by overexpression to cyclin D1. Oncogene 1998; 16:913-20.
43. T. C. Wang, R. D. Cardiff, L. Zukerberg, E. Lees, A. Arnold, E. V. Schmidt, Mammary hyperplasia and carcinoma in MMTV-cyclin D1 transgenic mice. Nature 1994; 369: 669-71.
44. C. J. Nelsen, D. G. Rickheim, N. A. Timchenko, M. W. Stanley, J. H. Albrecht. Transient expression of cyclin D1 is sufficient to promote hepatocyte replication and liver growth in vivo. Cancer Res 2001; 61:8564-68.
45. K. Nakayama, N. Ishida, M. Shirane, A. Inomata, T. Inoue, N. Shishido, I. Horii, D. Y. Loh, K. Nakayama, Mice lacking p27(Kip1) display increased body size, multiple organ hyperplasia, retinal dysplasia, and pituitary tumors. Cell 1996; 85:707-20.
46. T. Arato-Ohshima, H. Sawa, Over-expression of cyclin D1 induces glioma invasion by increasing matrix metalloproteinase activity and cell motility. Int J Cancer 1999: 83:387-92.
47. M. Drobnjak, I. Osman, H. I. Scher, M. Fazzari, C. Cordon-Cardo, Overexpression of cyclin D1 is associated with metastatic prostate cancer to bone. Clin Cancer Res 2000; 6:1891-95.
48. Khokhlatchev A, Rabizadeh S, Xavier R, Nedwidek M, Chen T, Zhang X F, Seed B, Avruch J. Identification of a novel Ras-regulated proapoptotic pathway. Curr Biol 2002; 12:253-65.
49. Lee K K, Ohyama T, Yajima N, Tsubuki S, Yonehara S. MST, a physiological caspase substrate, highly sensitizes apoptosis both upstream and downstream of caspase activation. J Biol Chem 2001; 276:19276-85.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

The invention claimed is:

1. A compound that has the structure:

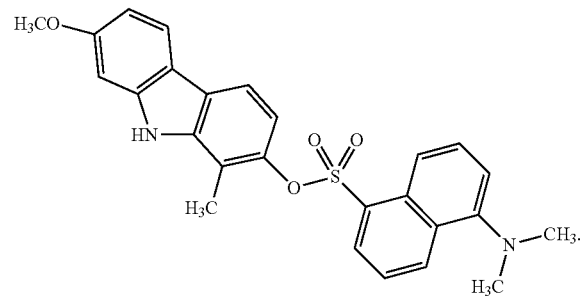 [SMILES: COc1ccc2c(c1)[nH]c1c(C)c(OS(=O)(=O)c3cccc4c(N(C)C)cccc34)ccc12]

2. A method for treating a cancer in a subject, the method comprising: administering to a subject in need of such treatment a therapeutically effective amount of a composition comprising the compound of claim 1 to treat the cancer in the subject.

3. The method of claim 2, wherein treatment suppresses further growth of the cancer.

4. The method of claim 2, wherein treatment results in regression of the cancer.

5. The method of claim 2, wherein the cancer comprises cancer cells with decreased Ras-association domain family IA (RASSF1A) expression.

6. The method of claim 5, wherein the Ras-association domain family IA (RASSF1A) expression is decreased by an increase in methylation of the promoter for RASSF1A.

7. The method of claim 5, wherein administration of the composition increases Ras-association domain family IA (RASSF1A) expression.

8. A method for suppressing the growth of a cell, the method comprising: contacting the cell with a composition comprising the compound of claim 1 to suppress the growth of the cell.

9. A method for reducing DNA methyltransferase activity in a cell, the method comprising: contacting the cell with a composition comprising the compound of claim 1 to reduce DNA methyltransferase activity in the cell.

10. The method of claim 9, wherein the DNA methyltransferase activity is reduced by reducing the activity of DNA methyltransferase 3b (DNMT-3b).

11. A method for increasing Ras-association family IA (RASSF1A) expression in a cell, the method comprising: contacting the cell with a composition comprising the compound of claim 1 to increase RASSF1A expression in the cell.

12. The method of claim 11, wherein the cell has decreased Ras-association domain family IA (RASSF1A) expression.

13. The method of claim 8, wherein the cell is a cancer cell.

14. A method of identifying a cell in which Ras-association domain family IA (RASSF1A) expression is decreased, the method comprising: contacting the cell with a composition comprising the compound of claim 1, wherein if the compound is retained in the cell, the cell is identified as having decreased RASSF1A expression.

15. A method of determining if one or more cells from a subject are cancer cells, the method comprising: obtaining one or more cells from a subject, contacting the one or more cells with a composition comprising the compound of claim 1, measuring the fluorescence of the one or more cells, wherein if the fluorescence of the one or more cells is indicative of the presence of the compound, the one or more cells is identified as being a cancer cell.

16. A pharmaceutical composition comprising the compound of claim 1 and a pharmaceutically acceptable carrier.

17. The pharmaceutical composition of claim 16, further comprising one or more additional anti-cancer compounds.

18. A kit comprising a pharmaceutical composition comprising a therapeutically effective amount of the compound of claim 1, and instructions for preparation and/or administration of the pharmaceutical composition.

19. The kit of claim 18, further comprising one or more additional anti-cancer compounds.

20. A prodrug of the compound of claim 1, wherein the prodrug comprises the compound and (a) a group attached to the compound as a carboxylate ester, wherein the group is alkyl, aryl, aralkyl, acyloxyalkyl, alkoxycarbonyloxyalkyl, or (b) a group attached to the compound as an ester of hydroxyl, thiol, or amine, wherein the group is an acyl group, an alkoxycarbonyl, aminocarbonyl, phosphate, or sulfate.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 1
cacacggact acaggggagt                                                   20

<210> SEQ ID NO 2
<211> LENGTH: 20
<212> TYPE: DNA
<213> ORGANISM: artificial sequence
<220> FEATURE:
<223> OTHER INFORMATION: synthetic oligonucleotide
```

```
<400> SEQUENCE: 2
aggaagcggt ccaggtagtt                                              20

<210> SEQ ID NO 3
<211> LENGTH: 24
<212> TYPE: DNA
<213> ORGANISM: artificial sequence
<220> FEATURE:
<223> OTHER INFORMATION: synthetic oligonucleotide

<400> SEQUENCE: 3
ccacccatgg caaattccat ggca                                         24

<210> SEQ ID NO 4
<211> LENGTH: 24
<212> TYPE: DNA
<213> ORGANISM: artificial sequence
<220> FEATURE:
<223> OTHER INFORMATION: synthetic oligonucleotide

<400> SEQUENCE: 4
tctagacggc aggtcaggtc cacc                                         24
```